US009678053B2

(12) United States Patent
Kato

(10) Patent No.: US 9,678,053 B2
(45) Date of Patent: Jun. 13, 2017

(54) LIQUID SENSOR COMPRISING FIRST AND SECOND ELECTRODES OPPOSING EACH OTHER

(71) Applicant: AISAN KOGYO KABUSHIKI KAISHA, Aichi-ken (JP)

(72) Inventor: Nobuhiro Kato, Aichi-ken (JP)

(73) Assignee: AISAN KOGYO KABUSHIKI KAISHA, Obu-Shi, Aichi-ken (JP)

( * ) Notice: Subject to any disclaimer, the term of this patent is extended or adjusted under 35 U.S.C. 154(b) by 255 days.

(21) Appl. No.: 14/500,780

(22) Filed: Sep. 29, 2014

(65) Prior Publication Data

US 2015/0090011 A1    Apr. 2, 2015

(30) Foreign Application Priority Data

Oct. 1, 2013  (JP) .................................. 2013-206648

(51) Int. Cl.
    *G01N 33/22*      (2006.01)
    *G01N 33/28*      (2006.01)

(52) U.S. Cl.
    CPC ................................ *G01N 33/2852* (2013.01)

(58) Field of Classification Search
    CPC .. G01N 33/2852; G01N 33/22; G01N 27/226; G01N 2/403
    See application file for complete search history.

(56) References Cited

U.S. PATENT DOCUMENTS

| 6,250,152 B1* | 6/2001 | Klein | G01F 23/268 |
| | | | 324/690 |
| 2005/0258839 A1* | 11/2005 | Gaignet | G01N 27/07 |
| | | | 324/696 |

(Continued)

FOREIGN PATENT DOCUMENTS

| JP | S63-243743 A | 10/1988 |
| JP | 2006-153840 A | 6/2006 |

(Continued)

OTHER PUBLICATIONS

English Abstract of Japanese Patent Application No. JP 2012-108030.

(Continued)

*Primary Examiner* — Francis Gray
(74) *Attorney, Agent, or Firm* — Vierra Magen Marcus LLP

(57) ABSTRACT

A liquid sensor may comprise a first electrode, a second electrode disposed inside the first electrode, and a partition wall comprising a surface defining a storage space with a first opposing surface of the first electrode and a second opposing surface of the second electrode. One of the first electrode, the second electrode and the partition wall may comprise a first communication opening communicating an inside of the storage space and an outside of the storage space and disposed at an upper portion of the storage space. One of the first electrode, the second electrode and the partition wall may comprise a second communication opening communicating the inside of the storage space and the outside of the storage space and disposed lower than the first communication opening. An opening direction of the first communication opening may be different from an opening direction of the second communication opening.

12 Claims, 24 Drawing Sheets

(56) References Cited

U.S. PATENT DOCUMENTS

| | | | |
|---|---|---|---|
| 2007/0243104 A1* | 10/2007 | Aoki | B41J 2/17566 422/400 |
| 2008/0006530 A1* | 1/2008 | Winarta | G01N 33/54386 204/403.01 |
| 2008/0217175 A1* | 9/2008 | Wells | G01N 27/401 204/435 |
| 2009/0173152 A1 | 7/2009 | Sato et al. | |
| 2009/0193873 A1 | 8/2009 | Nakamura | |
| 2010/0101307 A1 | 4/2010 | Sato et al. | |
| 2012/0126835 A1 | 5/2012 | Nakamura | |

FOREIGN PATENT DOCUMENTS

| | | |
|---|---|---|
| JP | 2006-317214 A | 11/2006 |
| JP | 2008-215954 | 9/2008 |
| JP | 2009-180159 | 8/2009 |
| JP | 2011-107070 | 6/2011 |
| JP | 2012-108030 | 6/2012 |

OTHER PUBLICATIONS

Machine Translation prepared by the Japanese Patent Office of Japanese Patent Application No. JP 2012-108030.

English Abstract of Japanese Patent Application No. JP 2009-180159.

Machine Translation prepared by the Japanese Patent Office of Japanese Patent Application No. JP 2009-180159.

English Abstract of Japanese Patent Application No. JP JP 2011-107070.

Machine Translation prepared by the Japanese Patent Office of Japanese Patent Application No. JP 2011-107070.

English Abstract of Japanese Patent Application No. JP 2008-215954.

Machine Translation prepared by the Japanese Patent Office of Japanese Patent Application No. JP 2008-215954.

Office Action dated Mar. 7, 2017 in Japanese Patent Application No. JP2013-206648.

* cited by examiner

US 9,678,053 B2

LIQUID SENSOR COMPRISING FIRST AND SECOND ELECTRODES OPPOSING EACH OTHER

CROSS-REFERENCE TO RELATED APPLICATION

This application claims priority to Japanese Patent Application No. 2013-206648 filed on Oct. 1, 2013, the contents of which are hereby incorporated by reference into the present application.

TECHNICAL FIELD

The present application discloses a liquid sensor comprising a first electrode and a second electrode opposing the first electrode.

DESCRIPTION OF RELATED ART

Japanese Patent Application Publication, No. 2012-108030 discloses a fuel sensor configured to detect a concentration of ethanol in fuel. The fuel sensor includes an outer electrode and an inner electrode. The outer electrode is disposed on a fuel passage. The inner electrode is disposed inside of the outer electrode. The outer electrode includes a communication opening through which fuel flowing through the fuel passage is introduced into a space between the outer electrode and the inner electrode. The fuel sensor is configured to detect the concentration of ethanol from an electrical characteristic between the outer electrode and the inner electrode.

SUMMARY

Liquid may contain bubbles. In a case where liquid between electrodes contains many bubbles, it is difficult to properly detect a property of the liquid with the electrodes. This specification provides a technology for properly discharging gas out of a space between electrodes.

The present application discloses a liquid sensor. The liquid sensor may comprise a first electrode, a second electrode, and a partition wall. The first electrode may comprise a first opposing surface. The second electrode may be disposed inside the first electrode. The second electrode may comprise a second opposing surface opposing the first opposing surface with a clearance in between. The partition wall may comprise a surface defining a storage space with the first opposing surface and the second opposing surface. One of the first electrode, the second electrode and the partition wall may comprise a first communication opening communicating an inside of the storage space and an outside of the storage space and disposed at an upper portion of the storage space. One of the first electrode, the second electrode and the partition wall may comprise a second communication opening communicating the inside of the storage space and the outside of the storage space and disposed lower than the first communication opening. An opening direction of the first communication opening may be different from an opening direction of the second communication opening.

In the foregoing configuration, liquid flows into the storage space through one of the first communication opening and the second communication opening and flows out of the storage space through the other one of the first communication opening and the second communication opening. Since the first communication opening is provided above the storage space, gas in the storage space is discharged out of the storage space through the first communication opening. Furthermore, since the second communication opening is provided below the first communication opening and the opening direction of the first communication opening is different from the opening direction of the second communication opening, the liquid flows from one of the first communication opening and the second communication opening to the other one of the first communication opening and the second communication opening in such a manner as to spread across the storage space. As a result of this, the liquid may be inhibited from staying inside of the storage space. This causes gas in the liquid to be discharged out of the storage space by being pushed out by the liquid. According to this configuration, the gas out of the clearance between electrodes may be properly discharged.

DETAILED DESCRIPTION

Figure 1:
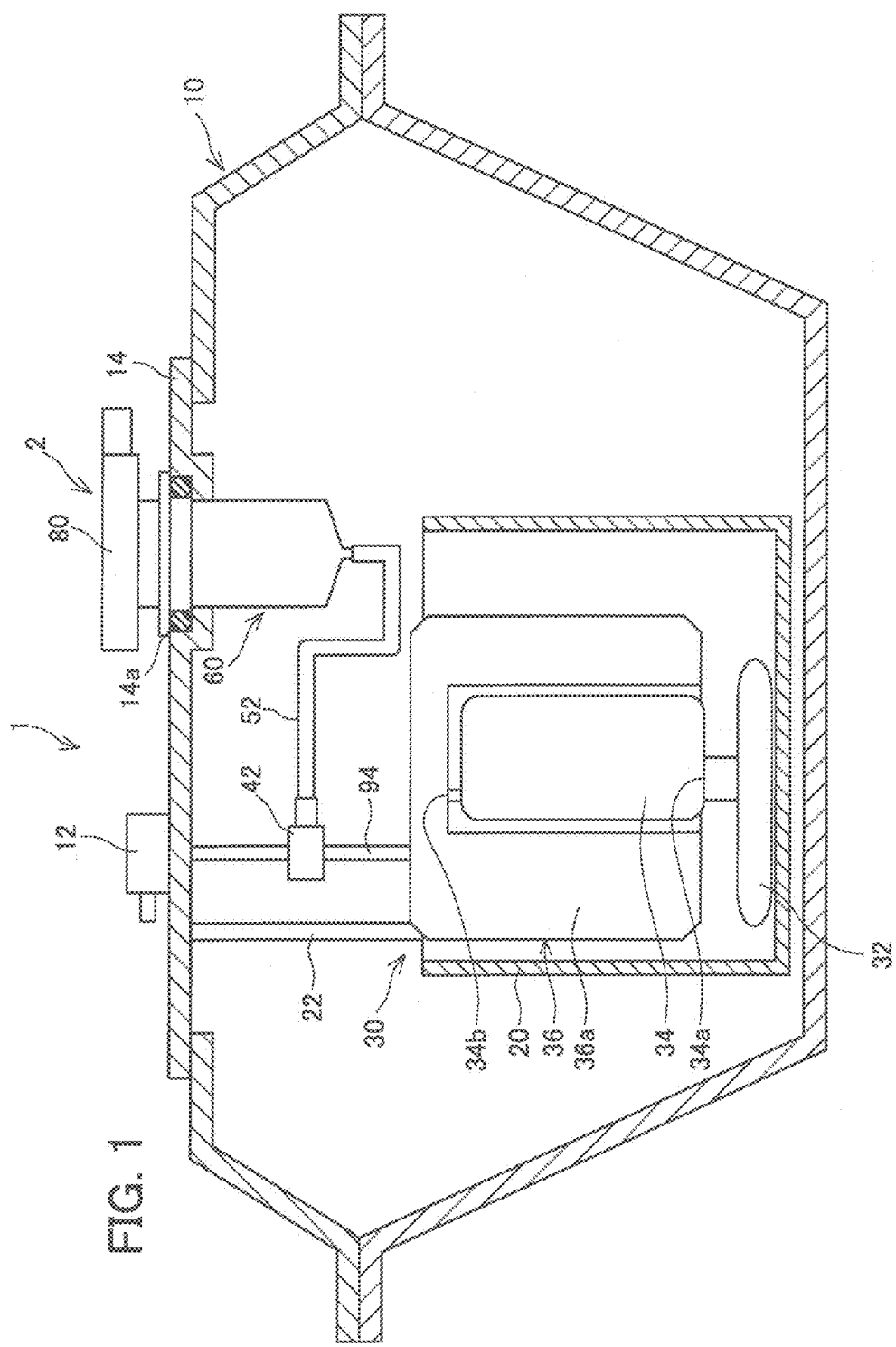
FIG. 1 shows a configuration of a fuel tank of a first embodiment and a peripheral area thereof.

Some features of embodiments described herein will be listed. Notably, technical features described herein are each independent technical element, and exhibit technical usefulness thereof solely or in combinations.

(Feature 1)

The liquid sensor may comprise an outer wall covering the first electrode from outside. This configuration allows the first electrode to be protected by the outer wall.

(Feature 2)

A clearance may be disposed between the outer wall and the first electrode. The outer wall may comprise a third communication opening communicating the clearance between the outer wall and the first electrode and an outside of the outer wall and disposed at an upper portion of the outer wall, and a fourth communication opening communicating between the clearance between the outer wall and the first electrode and the outside of the outer wall and disposed at a lower portion of the outer wall. Since the third communication opening is disposed at the upper portion of the outer wall, gas in liquid having flowed into the clearance between the outer wall and the first electrode is discharged out of the clearance between the outer wall and the first electrode through the third communication opening. Further, the liquid may flow into the clearance between the outer wall and the first electrode through one of the third communication opening and the fourth communication opening and flow out of the clearance between the outer wall and the first electrode through the other one of the third communication opening and the fourth communication opening. That is, the liquid moves between an upper end of and a lower end of the clearance between the outer wall and the first electrode. As a result of this, gas having entered the clearance between the outer wall and the first electrode may be discharged out of the clearance between the outer wall and the first electrode together with the liquid.

(Feature 3)

The clearance between the outer wall and the first electrode may communicate with the storage space via the first communication opening or the second communication opening, or a combination thereof. This configuration allows the liquid to flow through the clearance between the outer wall and the first electrode and the storage space.

(Feature 4)

The outer wall may comprise a dividing wall dividing the clearance between the outer wall and the first electrode into a plurality of sections and a fifth communication opening communicating the clearance between the outer wall and the first electrode and the outside of the outer wall. A first section of the plurality of sections may communicate with the outside of the outer wall via the fourth communication opening, with the storage space via the first communication opening, and with the outside of the outer wall via the third communication opening. A second section of the plurality of sections, being different from the first section, may communicate with the outside of the outer wall via the fifth communication opening, and with the storage space via the second communication opening. In this configuration, the liquid having flowed into the clearance between the outer wall and the first electrode through the fourth communication opening flows through the fourth communication opening, the first section, the first communication opening, the storage space, the second communication opening, the second section, and the fifth communication opening in this order, and is discharged out of the clearance between the outer wall and the first electrode. This configuration allows bubbles in the liquid having flowed into the clearance between the outer wall and the first electrode through the fourth communication opening to be discharged out of the clearance between the outer wall and the first electrode through the third communication opening. As a result, bubbles in the liquid that enter the storage space may be reduced.

(Feature 5)

The outer wall may be made of an electrically conductive material. This configuration allows the outer wall to be utilized as a shield electrode in the detection of a property of the liquid with the first electrode and the second electrode.

(Feature 6)

The partition wall may comprise an upper wall disposed at an upper end of the storage space. A surface of the upper wall defining the storage space may be inclined upward toward the first communication opening. This configuration allows gas having accumulated above the storage space to be guided toward the first communication opening.

(Feature 7)

The liquid sensor may comprise a temperature sensor configured to detect a temperature of liquid. According to this configuration, the temperature of the liquid in the storage space may be detected using the liquid sensor.

(Feature 8)

The temperature sensor may be disposed inside the second electrode and near the second communication opening. According to this configuration, a space in which the temperature sensor is disposed does not need to be provided separately. Further, the temperature of the liquid passing through the second communication opening may be detected.

(Feature 9)

A size of an external shape of one portion of the second electrode disposed near the second communication opening may be smaller than a size of an external shape of a portion of the second electrode other than the one portion of the second electrode. This configuration allows the temperature sensor to be closer to the liquid in the storage space. As a result of this, the temperature of the liquid in the storage space may be properly detected with the temperature sensor.

(Feature 10)

One of or both of the first electrode and the partition wall may comprise an opposing portion opposing the one portion of the second electrode disposed near the second communication opening. The opposing portion may have a shape formed along the external shape of the one portion of the second electrode disposed near the second communication opening. This configuration causes the liquid to smoothly flow near the one portion of the second electrode disposed near the second communication opening.

(Feature 11)

The first opposing surface and the second opposing surface may extend by being inclined relative to a vertical direction. The first opposing surface and the second opposing surface may extend horizontally.

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved liquid sensor, as well as methods for using and manufacturing the same.

Moreover, combinations of features and steps disclosed in the following detailed description may not be necessary to practice the invention in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

(First Embodiment)

A fuel feeding unit 1 of the present embodiment is mounted in an automobile, and feeds fuel to an engine (not illustrated). The fire supplying unit 1 includes a fuel tank 10, a fuel pump unit 30, and a sensor device 2. The fuel tank 10 retains gasoline or mixed fuel of gasoline and ethanol.

The fuel pump unit 30 includes a low-pressure filter 32, a pump body 34, a high-pressure filter 36, a reserve cup 20, a pressure regulator 42, and a discharge port 12. The low-pressure filter 32, the pump body 34, the high-pressure filter 36, the reserve cup 20, and the pressure regulator 42 are disposed inside of the fuel tank 10. The pump body 34 sucks the fuel stored in the fuel tank 10 through a suction opening 34a of the pump body 34 and pressurizes the fuel inside of the pump body 34. Then, the pump body 34 forces the pressurized fuel into a case 36a of the high-pressure filter 36 through an outlet 34b of the pump body 34.

The low-pressure filter 32 is formed in a bag shape by a nonwoven fabric. An inner part of the low-pressure filter 32 communicates with the suction opening 34a of the pump body 34. The high-pressure filter 36 includes the case 36a and a filter member (not illustrated). Although illustrated in a simplified manner in FIG. 1, the case 36a is disposed in such a manner as to extend circumferentially around the pump body 34. The fuel having flowed into the case 36a is filtered by the filter member of the high-pressure filter 36, and is sent out into a pipe 94. The pressure regulator 42 is connected to the pipe 94. The pressure regulator 42 releases an excess of the fuel inside of the pipe 94 into a release pipe 52 when the pressure of the fuel inside of the pressure regulator 42 becomes equal to or higher than a predetermined pressure, thereby adjusting the pressure of the fuel inside of the pipe 94 so that it is a constant pressure. The fuel stored in the fuel tank 10 has its pressure so adjusted by the pump body 34 and the pressure regulator 42 as to be a constant pressure, and is pumped through the discharge port 12 into the engine (not illustrated). The case 36a connects the outlet 34b of the pump body 34 and the pipe 94. The pipe 94 connects the outlet 34b of the pump body 34 and the discharge port 12.

The pump body 34, the low-pressure filter 32 and the high-pressure filter 36 are disposed inside of the reserve cup 20. The reserve cup 20 is fixed to a set plate 14 of the fuel tank 10 by a prop 22. A jet pump (not illustrated) sends the fuel outside of the reserve cup 20 into the reserve cup 20.

Figure 2:
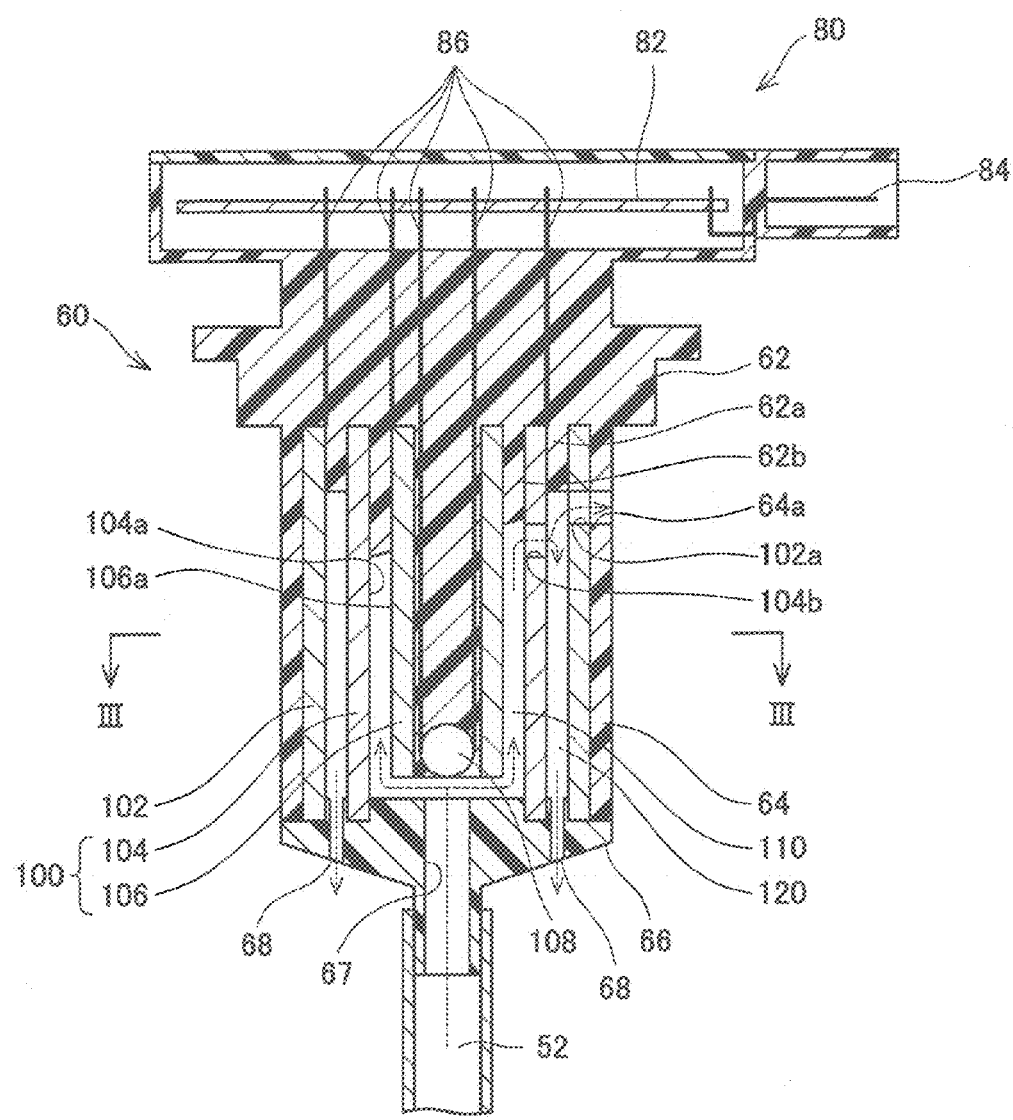
FIG. 2 shows a configuration of a liquid property sensor and control unit of the first embodiment.

The liquid level measuring device 2 includes a control device 80 and a liquid property sensor 60. The liquid property sensor 60 is fitted in an opening 14a in the set plate 14. That is, the liquid property sensor 60 is disposed at an upper portion of the fuel tank 10. As shown in FIG. 2, the liquid property sensor 60 includes an upper wall 62, a peripheral wall 64, a bottom wall 66, an electrode pair 100, an electrode 102, and a thermistor 108.

Figure 3:
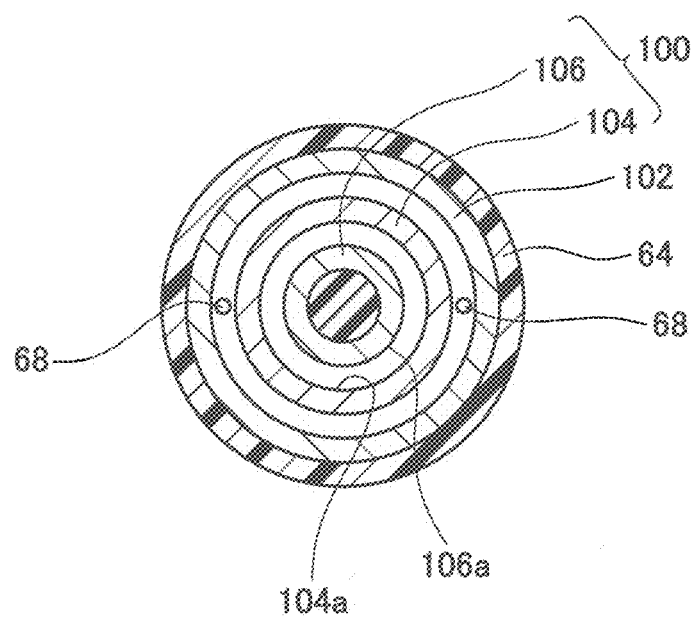
FIG. 3 shows a sectional view taken along cross-section III-III of FIG. 2.

The electrode pair 100 includes electrodes 104 and 106. Each of the electrodes 104 and 106 is made of a material having electric conductivity. The electrode 104 has a cylindrical shape (see FIG. 3). The central axis of the electrode 104 extends to a depth direction of the fuel tank 10. The electrode 104 has a communication opening 104b communicating an inside of the electrode 104 and an outside of the electrode 104 and disposed near an upper end of the electrode 104. The electrode 106 is disposed inside of the electrode 104. The electrode 106 has a cylindrical shape having the same central axis as the central axis of the electrode 104 (see FIG. 3). The length of the electrode 106 along its central axis is shorter than the length of the electrode 104 along its central axis. An upper end of the electrode 106 is located at the same level as the upper end of the electrode 104. The electrode 106 has an outer circumferential surface 106a entirely facing an inner circumferential surface of the electrode 104.

The electrode 106 is buried in resin so that no fuel enters an inside of the electrode 106. The thermistor 108 is disposed inside of the electrode 106. The thermistor 108 is covered with resin. The thermistor 108 is disposed at a lower end of the electrode 106. This configuration makes it unnecessary to separately secure a space in which the thermistor 108 is disposed.

The electrode 102 is disposed outside of the electrode 104. The electrode 102 has a cylindrical shape having the same central axis as the central axis of the electrode 104 (see FIG. 3). The length of the electrode 102 along its central axis is equal to the length of the electrode 102 along its central axis, and an upper end of the electrode 102 is located at the same level as the upper end of the electrode 104. The electrode 102 entirely covers the outer circumference of the electrode 104. This configuration allows the electrode 104 to be protected by the electrode 102. The electrode 102 has a communication opening 102a communicating an inside of the electrode 102 and an outside of the electrode 102 and disposed near the upper end of the electrode 102. The communication opening 102a is located above the communication opening 104b.

The electrode 102 has an outer circumferential surface entirely covered with the peripheral wall 64. The peripheral wall 64 is made of a non-conducting material such as resin. This configuration allows the electrode 102 to be protected by the peripheral wall 64. The peripheral wall 64 has a cylindrical shape having the same central axis as the central axis of the electrode 104 (see FIG. 3). The length of the peripheral wall 64 along its central axis is equal to the length of the electrode 102 along its central axis, and a lower end of the peripheral wall 64 is located at the same level as lower ends of the electrodes 102 and 104. The peripheral wall 64 has a communication opening 64a disposed in a place overlapping the communication opening 102a.

The upper wall 62 is disposed at an upper end of the peripheral wall 64. The upper wall 62 is molded integrally with the peripheral wall 64. The upper wall 62 is fitted in the opening 14a in the set plate 14 via an O-ring. A lower surface of the upper wall 62 is in contact with an upper end of the peripheral wall 64 and the upper ends of the electrodes 102, 104, and 106. The upper wall 62 includes support walls 62a and 62b each having a cylindrical shape extending downward from the lower surface of the upper wall 62.

The support wall 62a is disposed in a clearance between the electrodes 102 and 104. A lower end of the support wall 62a is located at the same level for the entire circumference thereof and located at substantially the same level as an upper end of the communication opening 102a. The support wall 62a supports the upper end of the electrode 102 by holding an upper portion of the electrode 102 together with the peripheral wall 64. The support wall 62b is disposed in a clearance between the electrodes 104 and 106. The support wall 62b supports the upper end of the electrode 104 by holding an upper portion of the electrode 104 together with the support wall 62a. Further, the support wall 62b supports the upper end of the electrode 106 by the electrode 106 being fitted inside of the support wall 62b. A lower end face of the support wall 62b is inclined upward toward the communication opening 104b, and is located at substantially the same level as the upper end of the communication opening 104b in a place overlapping the communication opening 104b circumferentially.

The bottom wall 66 is integrally attached to the lower end of the peripheral wall 64. The peripheral wall 64 is attached to an upper surface of the bottom wall 66. Further, lower portions of the electrodes 102 and 104 are inserted in the upper surface of the bottom wall 66. This causes the bottom wall 66 to support the lower ends of the electrodes 102 and 104. It should be noted that there is a clearance between the bottom wall 66 and the lower end of the electrode 106.

The bottom wall 66 has a communication opening 67 bored through the center thereof from a lower surface of the bottom wall 66 to the upper surface of the bottom wall 66. The communication opening 67 is disposed coaxially with the electrode 106 and faces the lower end of the electrode 106. The communication opening 67 communicates with the release pipe 52. Further, the bottom wall 66 has two communication openings 68 bored therethrough between the electrode 104 and the electrode 106 from the lower surface of the bottom wall 66 to the upper surface of the bottom wall 66. The lower surface of the bottom wall 66 is inclined downward from the outer circumference to the center.

A storage space 110 is defined by an opposing surface 104a, an opposing surface 106a, the upper wall 62, particularly a lower surface of the support wall 62b, and the upper surface of the bottom wall 66. Further, a storage space 120 is defined by an outer circumferential surface of the electrode 104, an inner circumferential surface of the electrode 102, the upper wall 62, particularly a lower surface of the support wall 62a, and the upper surface of the bottom wall 66. A lower end of the storage space 110 communicates with the release pipe 52 via the communication opening 67. An upper end of the storage space 110 communicates with the storage space 120 via the communication opening 104b. A lower end of the storage space 120 communicates an inside of the fuel tank 10 via the communication openings 68. An upper end of the storage space 120 communicates with the inside of the fuel tank 10 via the communication opening 102a and the communication opening 64a.

Fixed above the upper wall 62 is the control device 80. The control device 80 includes a control circuit 82 and an external terminal 84. The control circuit 82 supplied with electrical power via the external terminal 84. The control circuit 82 is mounted with a CPU, a memory, etc. The control circuit 82 is a circuit for detecting a temperature of fuel and a concentration of ethanol in fuel with the liquid property sensor 60. In other word, the liquid property sensor 60 is a liquid quality (i.e., the temperature of the liquid and the concentration of alcohol of the liquid) sensor controlled by the control circuit 82.

(Operation of Fuel Supplying Unit)

The fuel supplying unit 1 starts driving when a driver starts the automobile, for example, by turning on the ignition switch. Referring FIG. 1, when the fuel supplying unit 1 starts driving, the pump body 34 starts driving, and the fuel inside of the reserve cup 20 passes through the low-pressure filter 32 and is sucked through the suction opening 34a into the pump body 34. This configuration makes it possible to prevent the foreign matter from entering the pump body 34. The fuel inside of the pump body 34 is pressurized by an impeller provided in the pump body 34 and forced into the case 36a of the high-pressure filter 36 through the outlet 34b. Then, the fuel is supplied to the engine via the discharging port 12.

The pressure regulator 42 releases an excess of the fuel inside of the pipe 94 into the release pipe 52 when the pressure of the fuel inside of the pressure regulator 42 becomes equal to or higher than a predetermined pressure. As indicated by dashed arrows in FIG. 2, the fuel inside of the release pipe 52 flows into the storage space 110 through the communication opening 67. The fuel having flowed into the storage space 110 passes through a space between the opposing surface 104a and the opposing surface 106a along the outer circumference of the electrode 106. The fuel flows from bottom to top through the storage space 110 and flows out the storage space 110 into the storage space 120 through the communication opening 104b. A portion of the fuel having flowed into the storage space 120 is released out of the storage space 120 through the communication opening 102a and the communication opening 64a. The communication opening 102a and the communication opening 64a are disposed above the communication opening 104b. For this reason, gas discharged through the communication opening 104b along with the release of the fuel through the communication opening 104b is discharged out of the storage space 120 through the communication opening 102a and the communication opening 64a. Further, another portion of the fuel having flowed into the storage space 120 flows from top to bottom through the storage space 120 to be discharged out of the storage space 120 through the communication openings 68. This configuration allows the gas having flowed into the storage space 120 to be properly discharged out of the liquid property sensor 60, and also allows the fuel having flowed out of the storage space 110 through the communication opening 104b to be released downward. The lower surface of the bottom wall 66 is inclined downward from the outer circumference toward the center, i.e. from the communication openings 68 toward the communication opening 67. This configuration causes the fuel released out of the storage space 120 through the communication opening 68 to flow along the lower surface of the bottom wall 66. As a result of this, noise that is made by the fuel being released through the communication openings 68 can be reduced.

While the fuel supplying unit 1 is driven, the control circuit 82 detects the concentration of ethanol contained in the fuel stored in the fuel tank 10. The control circuit 82 repeats the detection of the concentration of ethanol until the engine of the automobile is stopped.

Specifically, the control circuit 82 converts the electric power, supplied from a battery (not illustrated) via a conducting wire 86, into a signal (i.e. an alternating current) of a predetermined frequency (e.g. 10 Hz to 3 MHz), and supplies the signal to the electrode 106. The control circuit 82 is also connected to the electrode 104. The signal supplied to the electrode 106 returns to the control circuit 82 from the electrode 104. As a result of this, charges are stored in the electrode pair 100, so that a capacitance is generated. The control circuit 82 calculates the capacitance of the electrode pair 100 using the signal having returned to the control circuit 82 from the electrode 104. Further, the control circuit 82 grounds the electrode 102 via the conducting wire 86. This causes the electrode 102 to function as a shield electrode. Then, the control circuit 82 supplies DC power to the thermistor 108 via the conducting wire 86 and detects the temperature of the thermistor 108 from the resistance value of the thermistor 108. The temperature of the thermistor 108 is substantially equal to the temperature of the fuel inside of the storage space 110. For this reason, the control circuit 82 can detect the temperature of the fuel inside of the storage space 110 by detecting the temperature of the thermistor 108.

Since a space between the electrodes 104 and 106 of the electrode pair 100 is filled with fuel, the capacitance of the electrode pair 100 fluctuates in a correlated way with the dielectric constant of the fuel. Since gasoline and ethanol differ greatly in dielectric constant from each other, the dielectric constant of the fuel changes depending on the concentration of ethanol. Further, the dielectric constant of the fuel also fluctuates in a correlated way with the temperature of the fuel. The control circuit 82 is mounted with a circuit for specifying the capacitance of the electrode pair 100 using the signal supplied to the electrode 106 and with a circuit for converting the capacitance thus specified into the dielectric constant of the fuel. Further, the control circuit 82 has stored therein a database for calculating the concentration of ethanol in the fuel from the dielectric constant of the fuel and from the temperature of the fuel. The database is specified in advance by experiment or by analysis. Upon obtaining the signal having returned to the control circuit 82 from the electrode 104, the control circuit 82 detects the concentration of ethanol in the fuel from the dielectric constant of the fuel with reference to the database. The control circuit 82 outputs the concentration of ethanol thus detected to an ECU (which is an abbreviation of "engine control unit"). The ECU adjusts, in accordance with the concentration of ethanol in the fuel, the amount of fuel that is to be supplied to the engine.

(Effects of the Present Embodiment)

In the liquid property sensor 60, the fuel flows into the storage space 110 through the communication opening 67 and flows out of the storage space 110 through the communication opening 104*b*. For this reason, the fuel moves between the upper end of the storage space 110 and a lower end of the storage space 110. Bubbles contained in the fuel move upward within the storage space 110 and are discharged out the storage space 110 through the communication opening 104*b* disposed near the upper end of the storage space 110. Furthermore, since the communication opening 67 is located at the lower end of the storage space 110 and the communication opening 104*b* is located at the upper end of the storage space 110 and since an opening direction of the communication opening 67 through which fuel flows in is different from an opening direction of the communication opening 104*b* through which fuel flows out, the fuel flows over the entire area within the storage space 110. As a result of this, the fuel can be inhibited from staying inside of the storage space 110. This causes gas in the storage space 110 to be discharged out of the storage space 110 by being pushed out by the fuel. This configuration makes it possible to properly discharge gas out of the storage space 110.

Further, the lower surface of the support wall 62*b* defining the upper end of the storage space 110 is inclined upward toward the communication opening 104*b*. This configuration allows gas having accumulated above the storage space 110 to be guided toward the communication opening 104*b*. This makes it possible to properly discharge gas out of the storage space 110.

(Correspondence Relationships)

In the present embodiment, the liquid property sensor 60, the electrode 104, the electrode 106, and the electrode 102 are an example of the "liquid sensor", an example of the "first electrode", an example of the "second electrode", and an example of the "outer wall", respectively. The opposing surface 104*a* is an example of the "first opposing surface", and the opposing surface 106*a* is an example of the "second opposing surface". The storage space 110 is an example of the "storage space", and the storage space 120 is an example of the "clearance between the outer wall and the first electrode". The support wall 62*b* of the upper wall 62 and the bottom wall 66 are an example of the "partition wall", and the lower surface of the support wall 62*b* is an example of the "surface of the upper wall defining the storage space". The communication opening 104*b*, the communication opening 67, the communication opening 102*b*, and the communication openings 68 are an example of the "first communication opening", an example of the "second communication opening", an example of the "third communication opening", and an example of the "fourth communication opening", respectively.

(Modifications of the First Embodiment)

Figure 4:
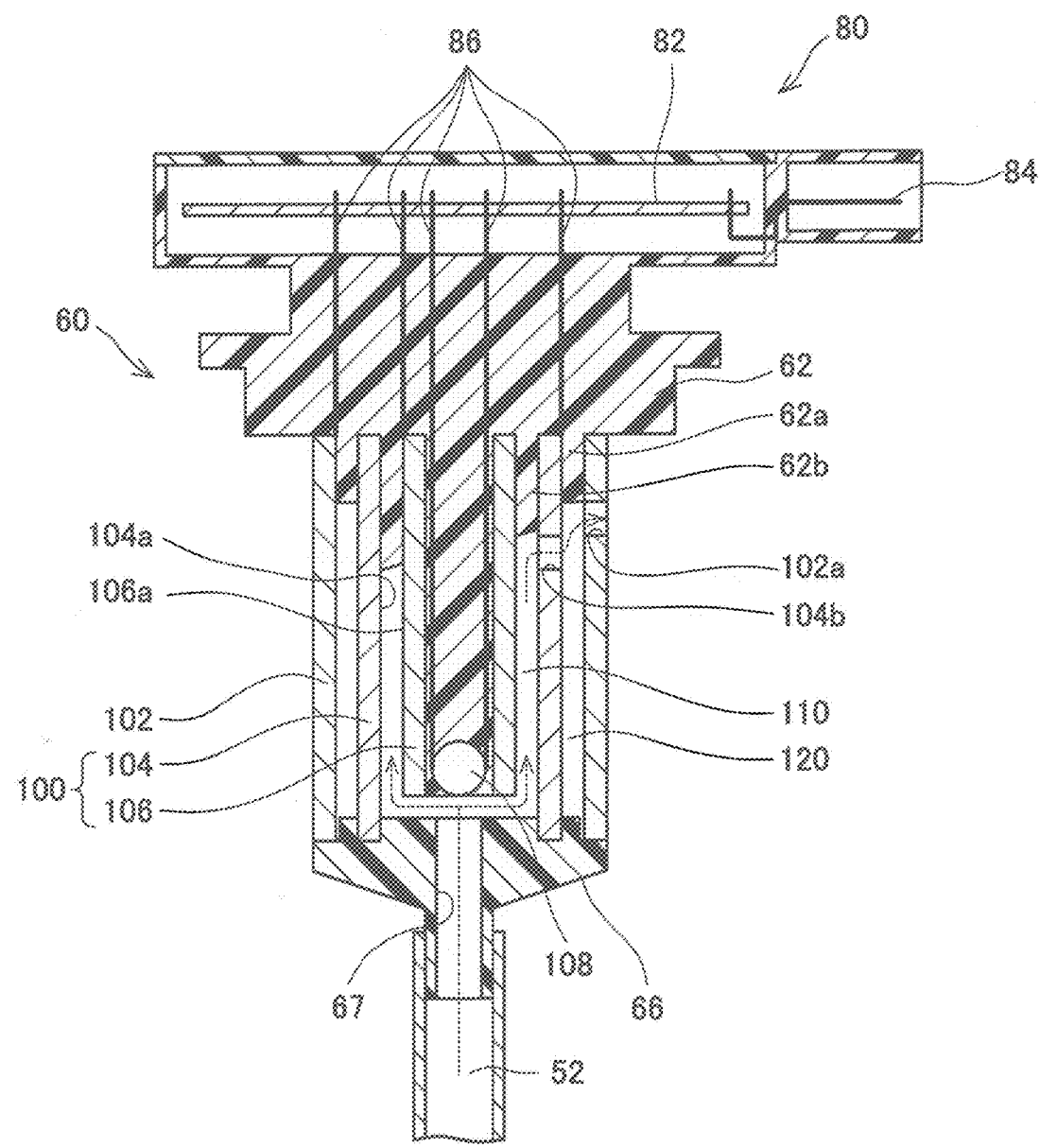
FIG. 4 shows a configuration of a liquid property sensor and control unit of a modification of the first embodiment.

(1) As shown in FIG. 4, the liquid property sensor 60 does not need to include the peripheral wall 64. Further, the bottom wall 66 does not need to have the communication openings 68. In this case, the fuel inside of the storage space 120 may flow out of the storage space 120 through the communication opening 102*a*.

Figure 5:
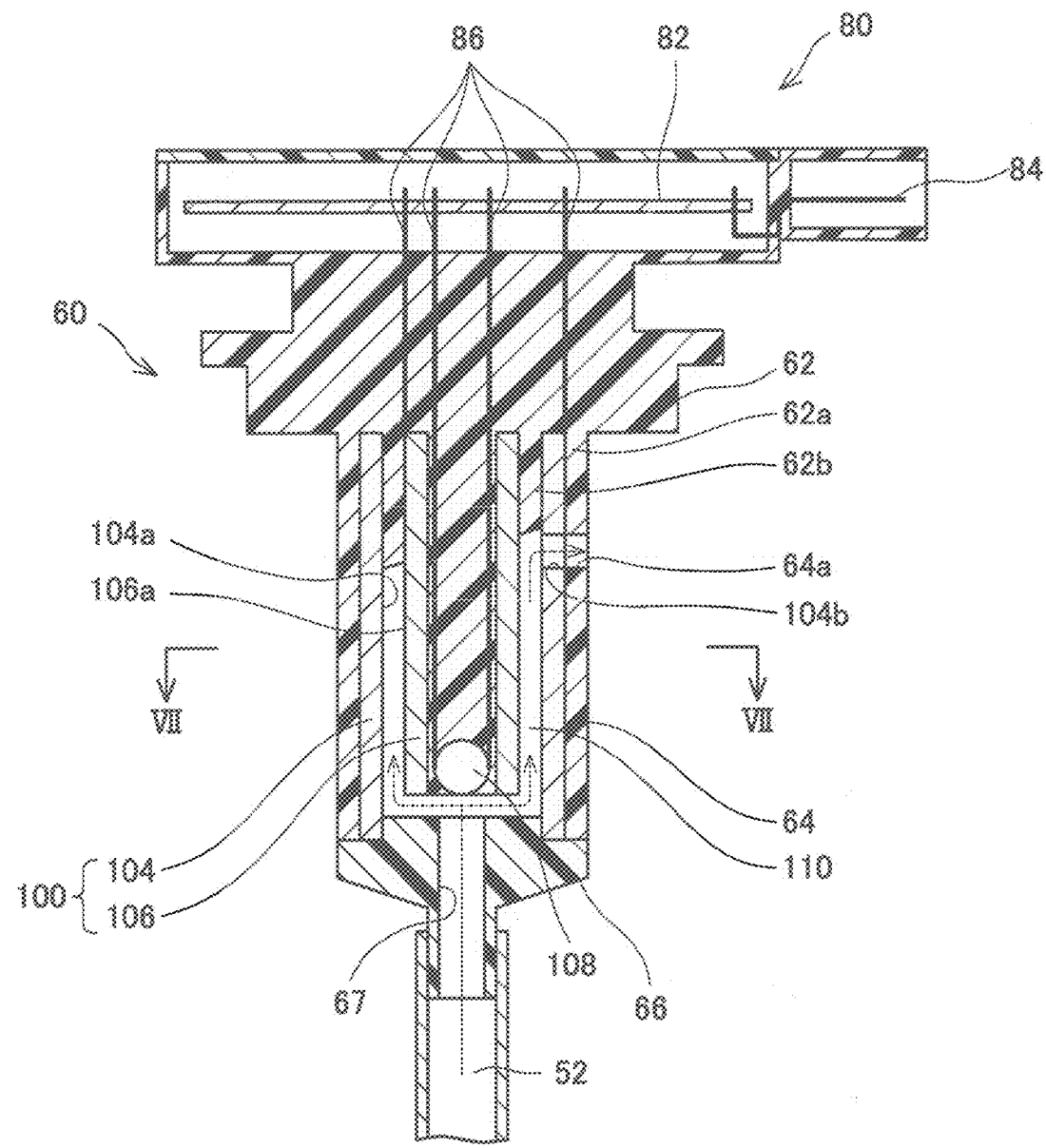
FIG. 5 shows a configuration of a liquid property sensor and control unit of a modification of the first embodiment.

(2) As shown in FIG. 5, the liquid property sensor 60 does not need to include the electrode 102. In this case, the peripheral wall 64 may entirely cover the outer circumferential surface of the electrode 104. Further, the fuel inside of the storage space 110 may flow out of the storage space 110 through the communication opening 104*b* and the communication opening 64*a*. In the present modification, the peripheral wall 64 is an example of the "outer wall".

Figure 6:
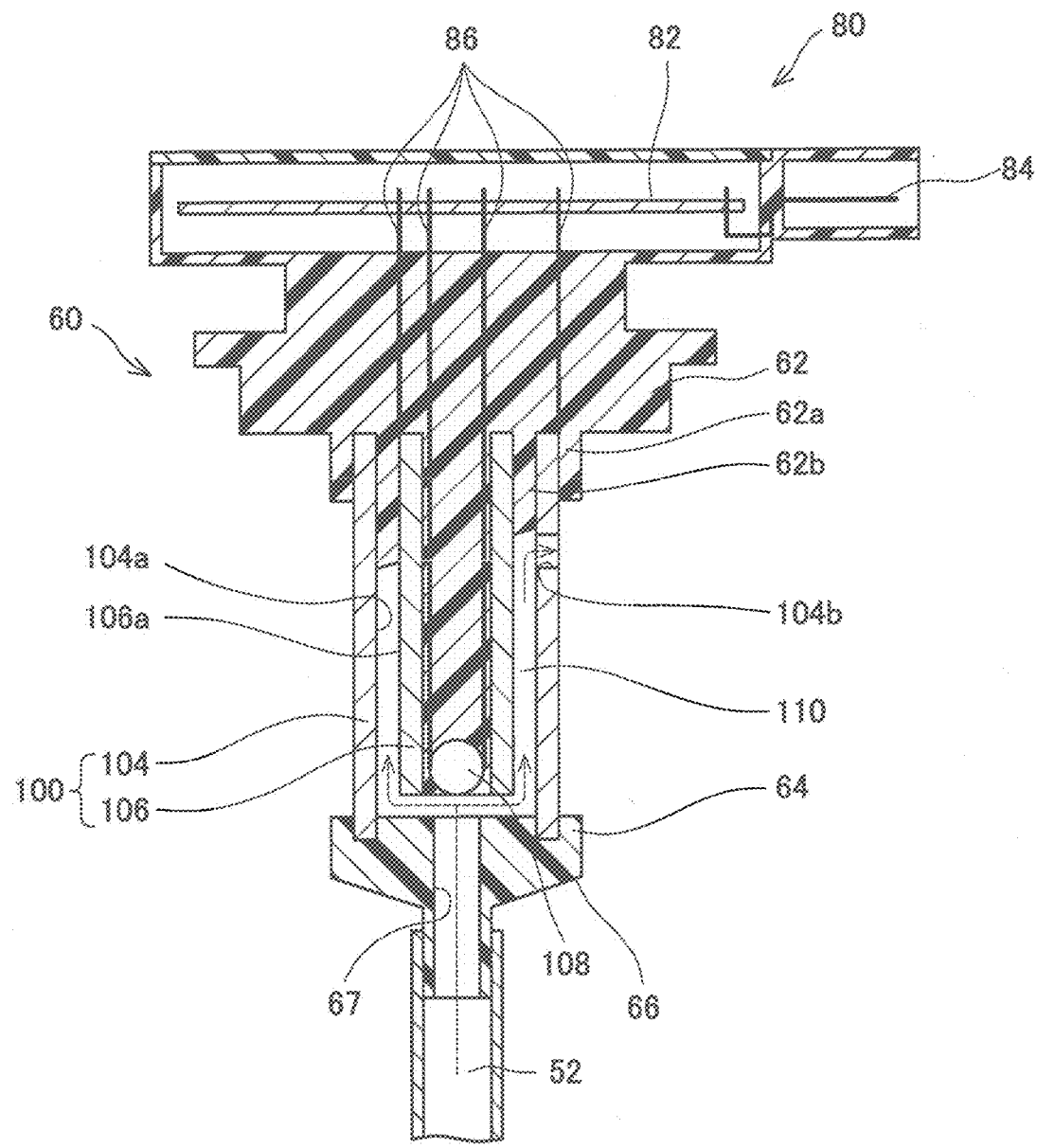
FIG. 6 shows a configuration of a liquid property sensor and control unit of a modification of the first embodiment.

(3) As shown in FIG. 6, as compared with FIG. 5, part of an outer circumferential surface of the electrode 104 may be exposed on the peripheral wall 64.

Figure 7:
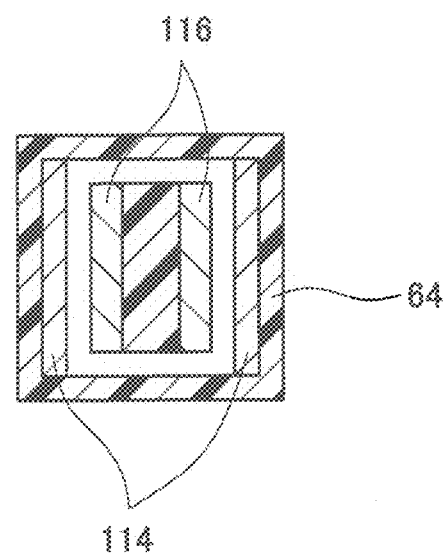
FIG. 7 shows a configuration of a liquid property sensor and control unit of a modification of the first embodiment, and a sectional view taken along cross-section VII-VII of FIG. 5.

(4) As shown in FIG. 7, the liquid property sensor 60 may include two electrode pairs 114 and 116 instead of including the electrodes 104 and 106 of FIG. 5. The electrode pair 114 may have a pair of flat electrodes. The electrode pair 116 may have a pair of flat electrodes. The electrode pair 116 may be disposed between the flat electrodes of the electrode pair 114. In this case, the peripheral wall 64 may be in the shape of a quadrangular tube. Further, each of the electrodes 104 and 106 may be in the shape of a polygonal tube instead of having a cylindrical shape.

Figure 8:
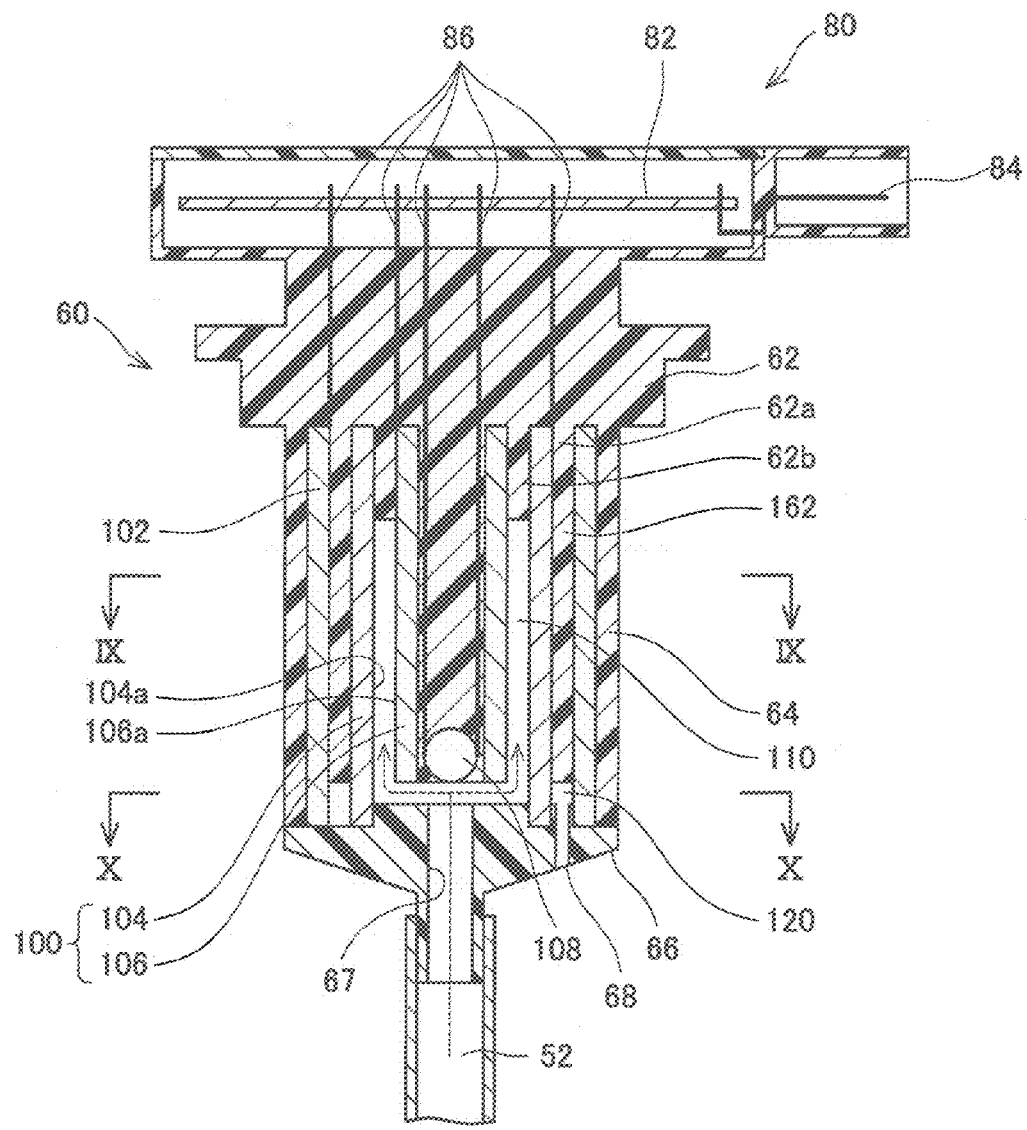
FIG. 8 shows a configuration of a liquid property sensor and control unit of a modification of the first embodiment.
Figure 9:
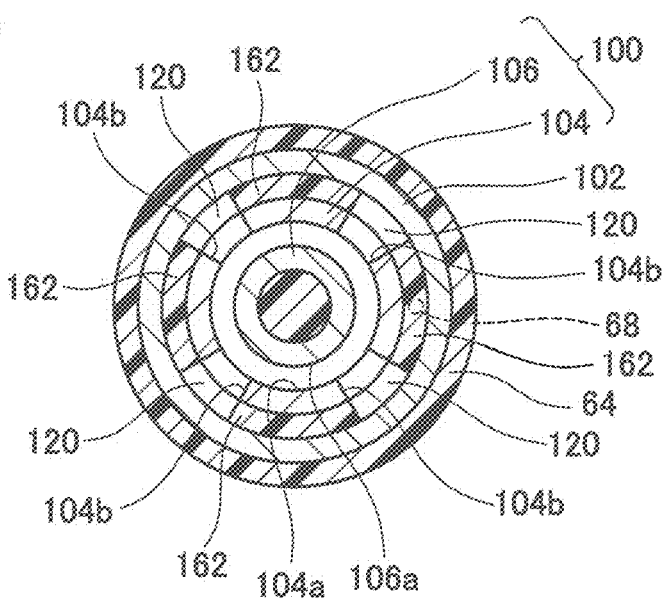
FIG. 9 shows a sectional view taken along cross-section IX-IX of FIG. 8.

(5) As shown in FIG. 8, a plurality of insulating layers 162 extending downward from the lower end of the support will 62a may be disposed between the electrode 102 and the electrode 104. The insulating layers 162 may be made of resin formed integrally with the support wall 62a. As shown in FIG. 9, the plurality of insulating layers 162 may be disposed at intervals within the storage space 120. In other words, the storage space 120 may be divided by the insulating layers 162 into a plurality of storage spaces 120. Each of the plurality of insulating layers 162 may be formed in an arc-like shape, extend downward from the lower end of the support wall 62a, and be disposed with a clearance between that insulating layer 162 and the bottom wall 66. In the electrode 104, a plurality of communication openings 104b may be disposed for each separate storage space 120 between adjacent insulating layers 162 so as to communicate that storage space 120 and the inside of the electrode 104.

Figure 10:
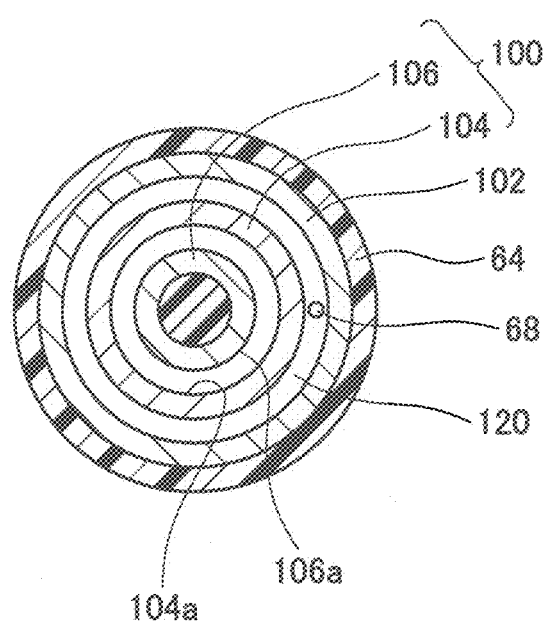
FIG. 10 shows a sectional view taken along cross-section X-X of FIG. 8.

As shown in FIG. 10, the storage space 120 is not divided by the insulating layers 162 below lower ends of the insulating layers 162, and may be entirely circumscribed between the electrode 102 and the electrode 104.

The configuration of the present modification makes it possible to inhibit the capacitance, i.e., stray capacitance, between the electrode 102 and the electrode 104 from changing depending on the dielectric constant of the fuel, and also to inhibit a leak current between the electrode 102 and the electrode 104. This makes it possible to reduce a detection error of the sensor device 2. Further, since the plurality of storage spaces 120 communicate with each other at the lower ends of the plurality of storage spaces 120, the plurality of communication openings 68 do not need to be disposed.

Figure 11:
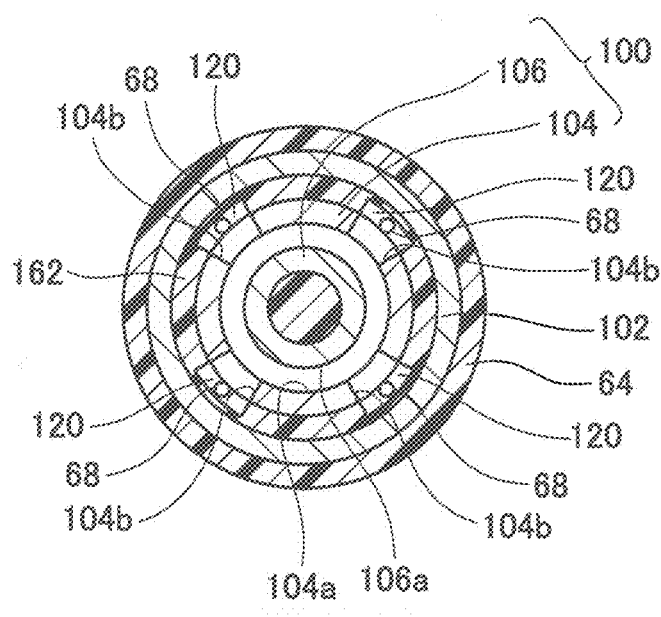
FIG. 11 shows a configuration of a liquid property sensor of a modification of the first embodiment, and a sectional view taken along cross-section identical with the cross-section IX-IX of FIG. 8.

(6) As shown in FIG. 11, as compared with the modifications of FIGS. 8 through 10 above, the plurality of insulating layers 162 disposed between the electrode 102 and the electrode 104 may entirely circumscribe the inner circumferential surface of the electrode 102. Further, the plurality of insulating layers 162 may be coupled to the upper surface of the bottom wall 66. That is, the storage space 120 may be divided by the plurality of insulating layers 162 into a plurality of storage spaces 120 that do not communicate with each other. In this case, the communication openings 68 may be provided at the respective lower ends of the plurality of storage spaces 120. The present modification can more properly prevent a leak current between the electrode 102 and the electrode 104. Further, since the communication openings 68 are disposed for the plurality of storage spaces 120, respectively, the fuel between the electrode 102 and the electrode 104 can be inhibited from staying therein.

Figure 12:
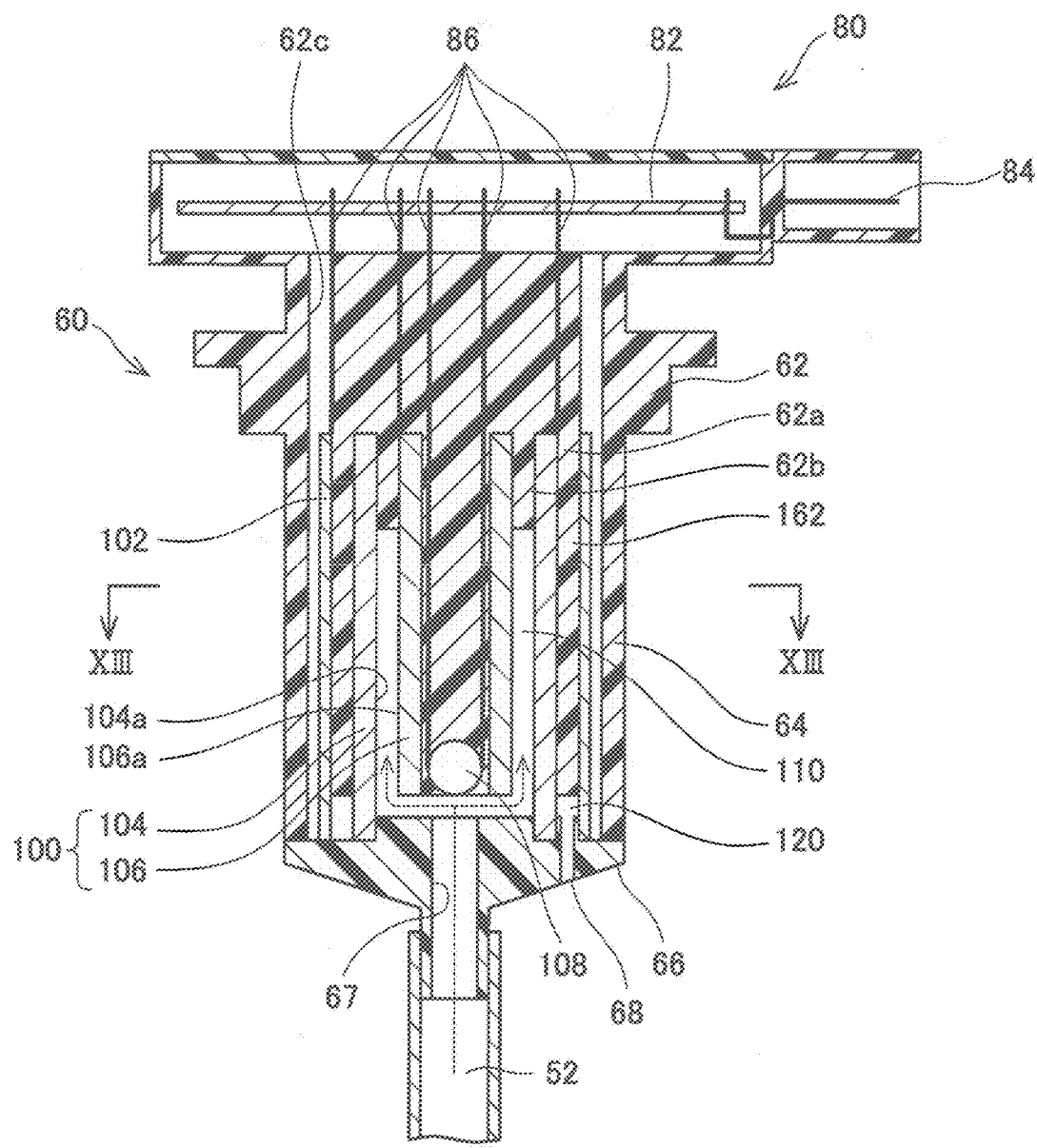
FIG. 12 shows a configuration of a liquid property sensor and control unit of a modification of the first embodiment.
Figure 13:
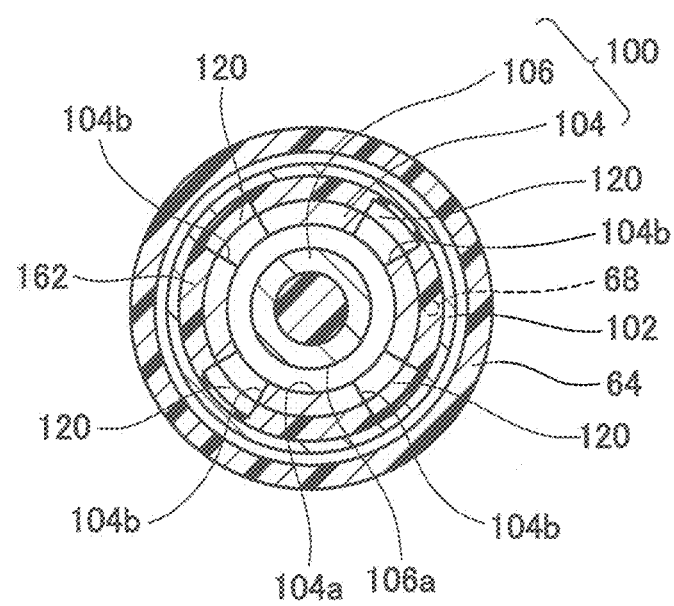
FIG. 13 shows a sectional view taken along cross-section of FIG. 12.

(7) As shown in FIGS. 12 and 13, as compared with the modifications of FIGS. 8 through 10 above, the outer circumferential surface of the electrode 102 may be disposed at a distance from an inner circumferential surface of the peripheral wall 64. Further, in the upper wall 62, an annular insertion space 62c vertically bored therethrough may be disposed. The electrode 102 may be passed through the insertion space 62c to be disposed between the peripheral wall 64 and the insulating layers 162. The configuration of the present modification makes it possible to dispose the electrode 102 after molding resin into the upper wall 62, the peripheral wall 64, etc., i.e. makes insert molding of the electrode 102 unnecessary. With the configuration of the present modification, resin molded articles such as the upper wall 62 and the peripheral wall 64 can be utilized with no electrode 102 disposed, for example, also in a case where there is no need to dispose a shield electrode to cause the electrode 104 to be grounded. That is, the configuration of the present modification makes it possible to commonly utilize the resin molded articles, such as the upper wall 62 and the peripheral wall 64, both in a configuration in which a shield electrode is needed and a configuration in which no shield electrode is needed. It should be noted that as shown in FIG. 13, the plurality of insulating layers 162 may be coupled in the same manner as that shown in FIG. 11.

(Second Embodiment)

Figure 14:
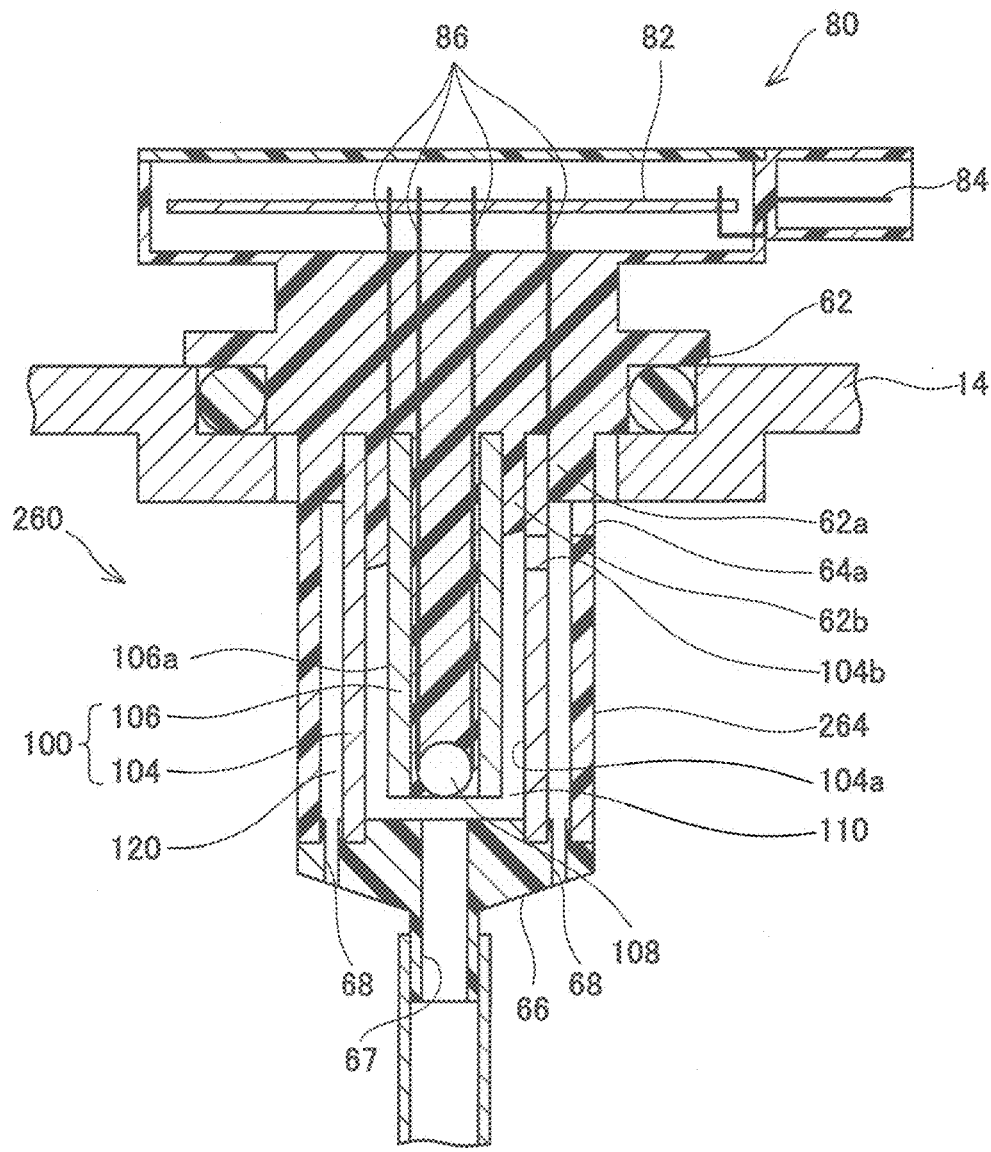
FIG. 14 shows a configuration of a liquid property sensor and control unit of a second embodiment.

Points of difference between a liquid property sensor 260 of the second embodiment and the liquid property sensor 60 of the first embodiment are described with reference to FIG. 14. Components that are the same as those of the first embodiment are given the same reference signs as those of the first embodiment.

The liquid property sensor 260 includes an upper wall 62, a peripheral wall 264, a bottom wall 66, an electrode pair 100, and a thermistor 108. It should be noted that the liquid property sensor 260 does not include an electrode 102.

The peripheral wall 264 is disposed with a clearance between the peripheral wall 264 and the outer circumferential surface of the electrode 104. Otherwise, the peripheral wall 264 is the same in configuration as the peripheral wall 64. The support wall 62a disposed on the lower surface of the upper wall 62 is disposed between the electrode 104 and the peripheral wall 264. The storage space 120 is defined by the outer circumferential surface of the electrode 104, the inner circumferential surface of the peripheral wall 264, the upper wall 62, particularly the lower surface of the support wall 62a, and the upper surface of the bottom wall 66.

(Third Embodiment)

Figure 15:
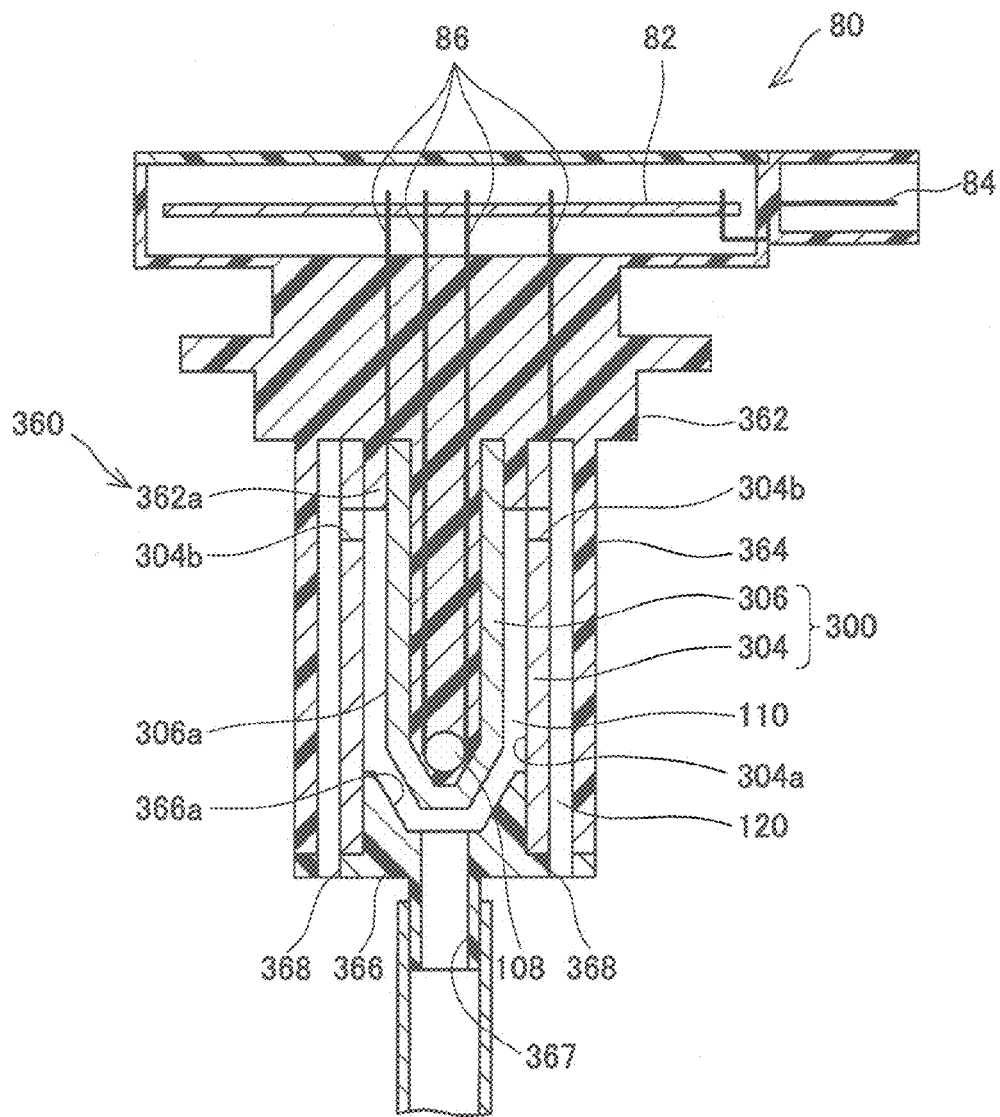
FIG. 15 shows a configuration of a liquid property sensor and control unit of a third embodiment.

Points of difference between a liquid property sensor 360 of the third embodiment and the second embodiment are described with reference to FIG. 15. Components that are the same as those of the second embodiment are given the same reference signs as those of the second embodiment. The liquid property sensor 360 includes an upper wall 362, a peripheral wall 364, a bottom wall 366, an electrode pair 300, and a thermistor 108.

The electrode pair 300 includes electrodes 304 and 306. As compared with the electrode 106, the electrode 306 has its lower portion becoming gradually narrower toward a lower position. Otherwise, the electrode 306 is the same in configuration as the electrode 106. This configuration allows the thermistor 108 to be closer to the liquid inside of the storage space 110. As a result of this, the temperature of the fuel inside of the storage space 110 can be more properly detected with the thermistor 108. The electrode 304 has two communication openings 304b communicating the storage space 110 and the storage space 120. Otherwise, the electrode 304 is the same in configuration as the electrode 104.

The upper wall 362 includes a support wall 362a, which corresponds to the support wall 62b, but does not include a support wall that corresponds to the support wall 62a. Otherwise, the upper wall 362 is the same in configuration as the upper wall 62. The peripheral wall 364 does not include a communication opening that corresponds to the communication opening 64a, i.e. a communication opening bored through the side wall 364 and communicating an inside of the storage space 120 and an outside of the storage space 120. Otherwise, the peripheral wall 364 is the same in configuration as the peripheral wall 264. A lower surface of the bottom wall 366 is an annular flat surface. The bottom wall 366 includes communication openings 368, which correspond to the communication openings 68, and a communication opening 367, which corresponds to the communication opening 67. A portion of an upper surface of the bottom wall 366 that faces the lower portion of the electrode 306 is a surface 366a that is inclined in parallel with the lower portion of the electrode 306. Otherwise, the bottom wall 366 is the same in configuration as the bottom wall 66.

The storage space 110 is defined by an opposing surface 304*a* of the electrode 304, an opposing surface 306*a* of the electrode 306, the upper wall 362, particularly a lower surface of the support wall 362*a*, and the upper surface of the bottom wall 366, and the storage space 120 is defined by an outer circumferential surface of the electrode 304, an inner circumferential surface of the peripheral wall 364, a lower face of the upper wall 362, and the upper surface of the bottom wall 366.

Fuel flows from the release pipe 52 into the storage space 110 through the communication opening 367. Since the lower portion of the electrode 306 that faces the communication opening 367 is inclined and the surface 366*a* of the bottom wall 366 has a shape along the lower portion of the electrode 306, the fuel can smoothly flow into the storage space 110 through the communication opening 367. As a result of this, the fuel can be inhibited from staying near the communication opening 367. The fuel having flowed into the storage space 110 flows into the storage space 120 through the communication opening 304*b* and flows out through the communication openings 368.

(Modification of the Third Embodiment)

Figure 16:
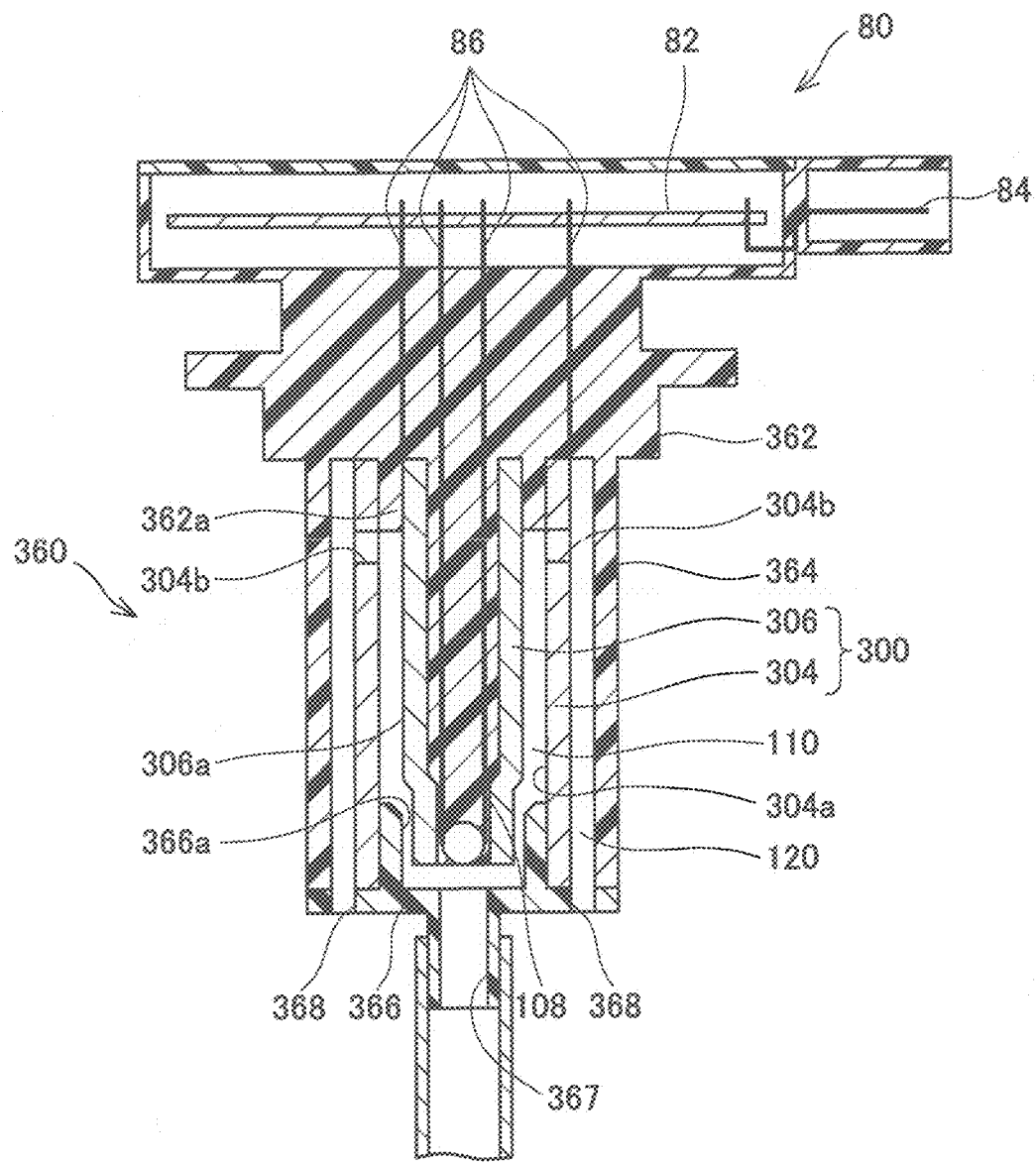
FIG. 16 shows a configuration of a liquid property sensor and control unit of a modification of the third embodiment.

The shape of the electrode 306 and the shape of the surface 366*a* of the bottom wall 366 are not limited to the aforementioned shapes. For example, the shape of the electrode 306 and the shape of the surface 366*a* of the bottom wall 366 may be shapes shown below in FIGS. 16 through 18. In FIG. 16, the lower portion of the electrode 306 may have a cylindrical shape that is smaller in diameter than an upper portion of the electrode 306. Furthermore, the electrode 306 may have an inclined surface that gradually changes in diameter. The surface 366*a* of the bottom wall 366 may be parallel to an outer circumferential surface of the lower portion of the electrode 306.

Figure 17:
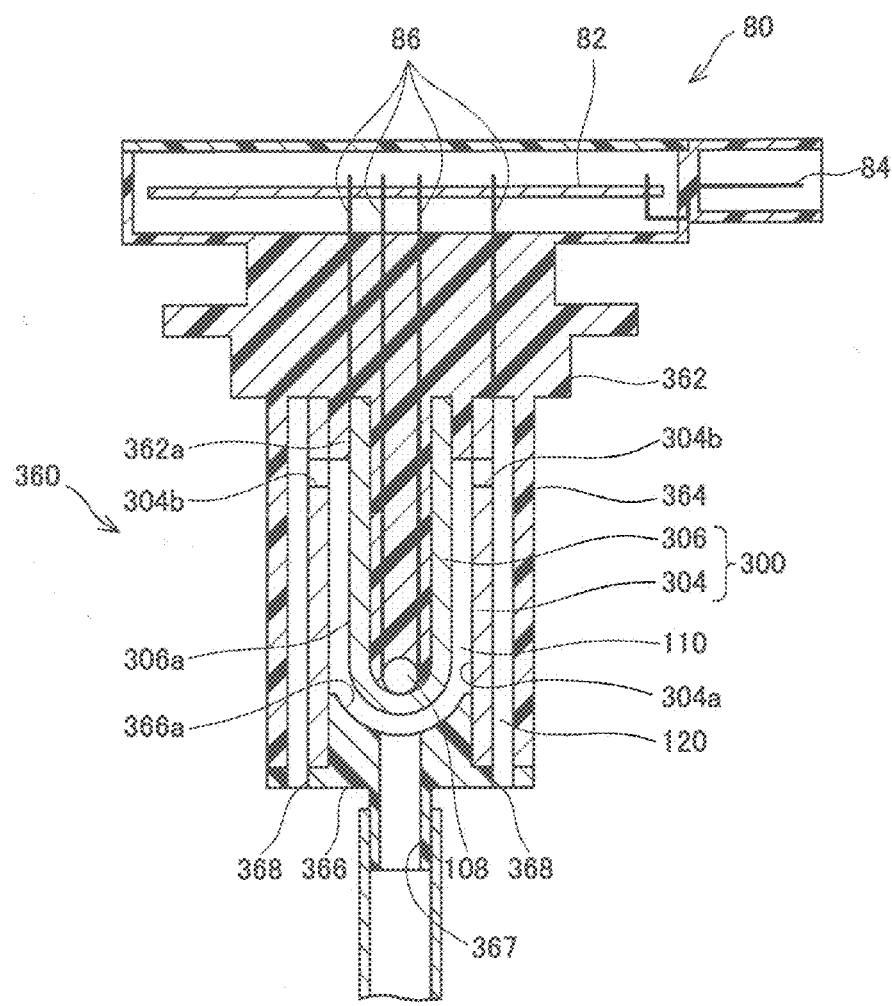
FIG. 17 shows a configuration of a liquid property sensor and control unit of a modification of the third embodiment.
Figure 18:
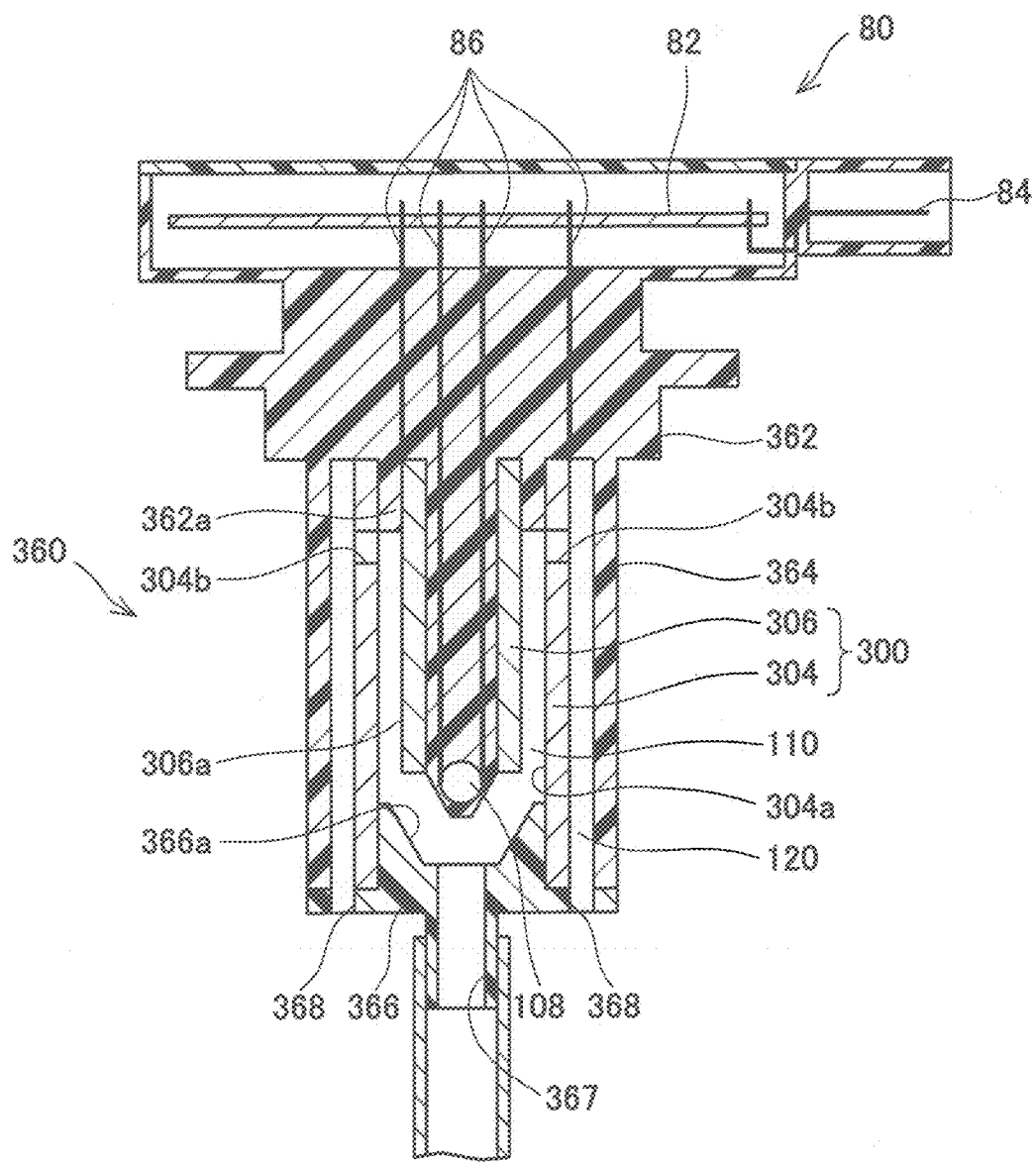
FIG. 18 shows a configuration of a liquid property sensor and control unit of a modification of the third embodiment.

As shown in FIG. 17, the lower portion of the electrode 306 may be in a semispherical shape. The surface 366*a* of the bottom wall 366 may be parallel to the outer circumferential surface of the lower portion of the electrode 306. It should be noted that the diameter of the semispherical shape of the lower portion of the electrode 306 may be smaller than the diameter of the cylindrical shape of the electrode 306. Alternatively, as shown in FIG. 18, resin surrounding the thermistor 108 may be exposed at the lower end of the electrode 306. In this case, the resin surrounding the thermistor 108 may become gradually narrower toward a lower position.

(Fourth Embodiment)

Figure 19:
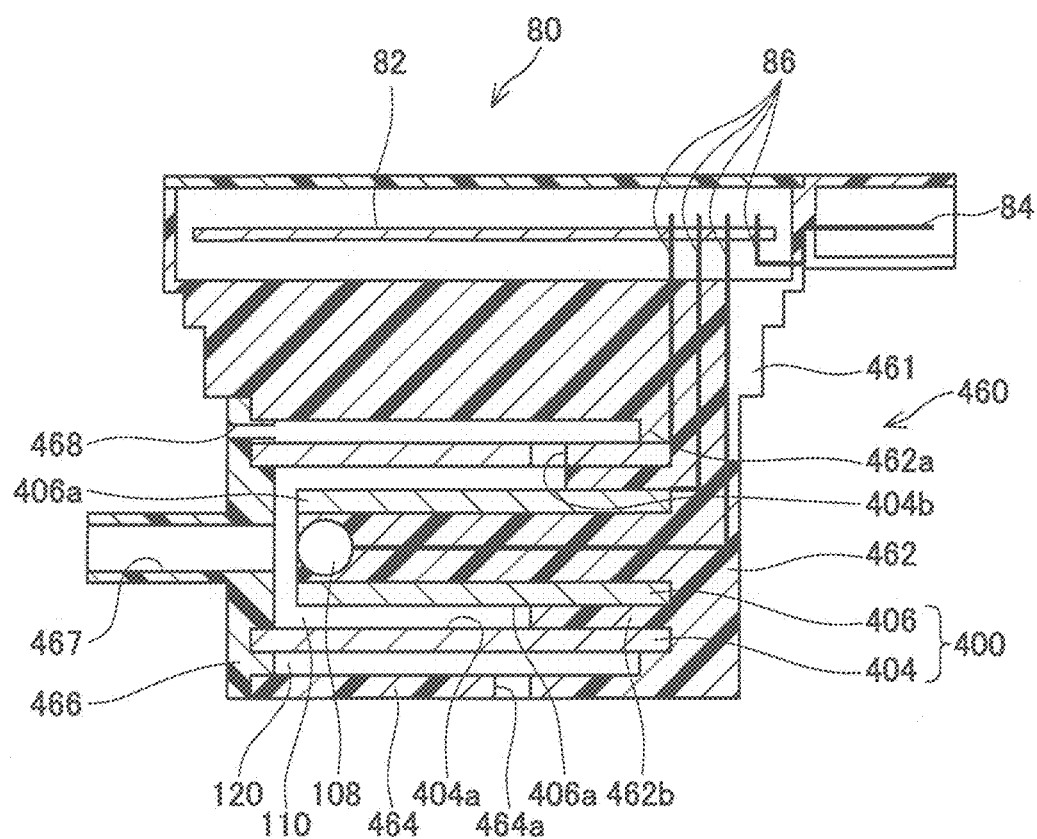
FIG. 19 shows a configuration of a liquid property sensor and control unit of a fourth embodiment.

Points of difference between a liquid property sensor 460 of the fourth embodiment and the second embodiment are described with reference to FIG. 19. Components that are the same as those of the second embodiment are given the same reference signs as those of the second embodiment. The liquid property sensor 460 includes an electrode pair 400, an upper wall 461, a peripheral wall 464, side walls 462 and 466, and a thermistor 108.

The electrode pair 400 includes electrodes 404 and 406. The electrodes 404 and 406 are disposed so that their central axes are parallel to the set plate 14 (see FIG. 1). Otherwise, the electrodes 404 and 406 are the same in configuration as the electrodes 104 and 106. It should be noted that a communication opening 404*a* in the electrode 404, i.e. a communication opening 404*b* communicating the storage space 110 and the storage space 120, is located at an upper end of the electrode 404.

As with the electrodes 404 and 406, the peripheral wall 464 is disposed so that its central axis is parallel to the set plate 14 (see FIG. 1). Disposed at an upper end of the peripheral wall 464 is the upper wall 461. The upper wall 461 is formed integrally with the peripheral wall 464. Otherwise, the peripheral wall 464 is the same in configuration as the peripheral wall 264. It should be noted that a communication opening 464*a* in the peripheral wall 464, i.e. a communication 464*a* communicating the inside of the storage space 120 and the outside of the storage space 120, is located at a lower end of the peripheral wall 464. The upper wall 461 is set in the opening 14*a* in the set plate 14 (see FIG. 1). Disposed on a lower surface of the upper wall 461 is the peripheral wall 464.

The side wall 462 is disposed at an end of the peripheral wall 464. The side wall 462 is formed integrally with the peripheral wall 464. One surface of the side wall 462 is in contact with one end of the peripheral wall 464 and one end of each of the electrodes 404 and 406. Disposed on the one surface of the side wall 462 are support walls 462*a* and 462*b* each having a cylindrical shape. The support wall 462*a* is disposed in a clearance between the peripheral wall 464 and the electrode 404. The support wall 462*b* is disposed in a clearance between the electrodes 404 and 406. The support wall 462*b* supports the upper end of the electrode 404 by holding the one end of the electrode 404 together with the support wall 462*a*. Further, the support wall 462*b* supports the one end of the electrode 406 by the electrode 406 being fitted inside of the support wall 462*b*. An end face of the support wall 462*b* is inclined closer to the side wall 462 toward the communication opening 404*b*.

The side wall 466 is attached integrally to the other end of the peripheral wall 464. The peripheral wall 464 is attached integrally to one surface of the side wall 466. Further, the other end of the electrode 404 is inserted in the one surface of the side wall 466. This causes the side wall 466 to support the other end of the electrode 404. It should be noted that there is a clearance between the peripheral wall 466 and the other end of the electrode 406.

The side wall 466 has a communication opening 467 bored through the center thereof. The communication opening 467 is disposed coaxially with the electrode 406 and faces the lower end of the electrode 406. The communication opening 467 communicates with the release pipe 52. Further, the side wall 466 has a communication opening 468 bored therethrough between the electrode 406 and the peripheral wall 464. The communication opening 468 is disposed at an upper end of the side wall 466.

The storage space 110 is defined by an opposing surface 404*a* of the electrode 404, an opposing surface 406*a* of the electrode 406, the one surface of the side wall 462, and the one surface of the side wall 466. Further, the storage space 120 is defined by an outer circumferential surface of the electrode 404, an inner circumferential surface of the peripheral wall 464, the one surface of the side wall 462, and the one surface of the side wall 466. A left end of the storage space 110 communicates with the release pipe 52 via the communication opening 467. The upper end of the storage space 110 communicates with the storage space 120 via the communication opening 404*b*. The lower end of the storage space 120 communicates with the outside of the storage space 120 via the communication opening 464*a*, and the upper end of the storage space 120 communicates with the outside of the storage space 120 via the communication opening 468.

The configuration of the present embodiment causes the fuel inside of the storage space 110 to flow substantially horizontally from the communication opening 467 to the communication opening 404b. As a result of this, the fuel inside of the storage space 110 can be comparatively smoothly delivered to the communication opening 404b. Further, since the communication opening 404b opens upward, gas in the storage space 110 can be easily discharged out of the storage space 110 through the communication opening 404b.

(Fifth Embodiment)

Figure 20:
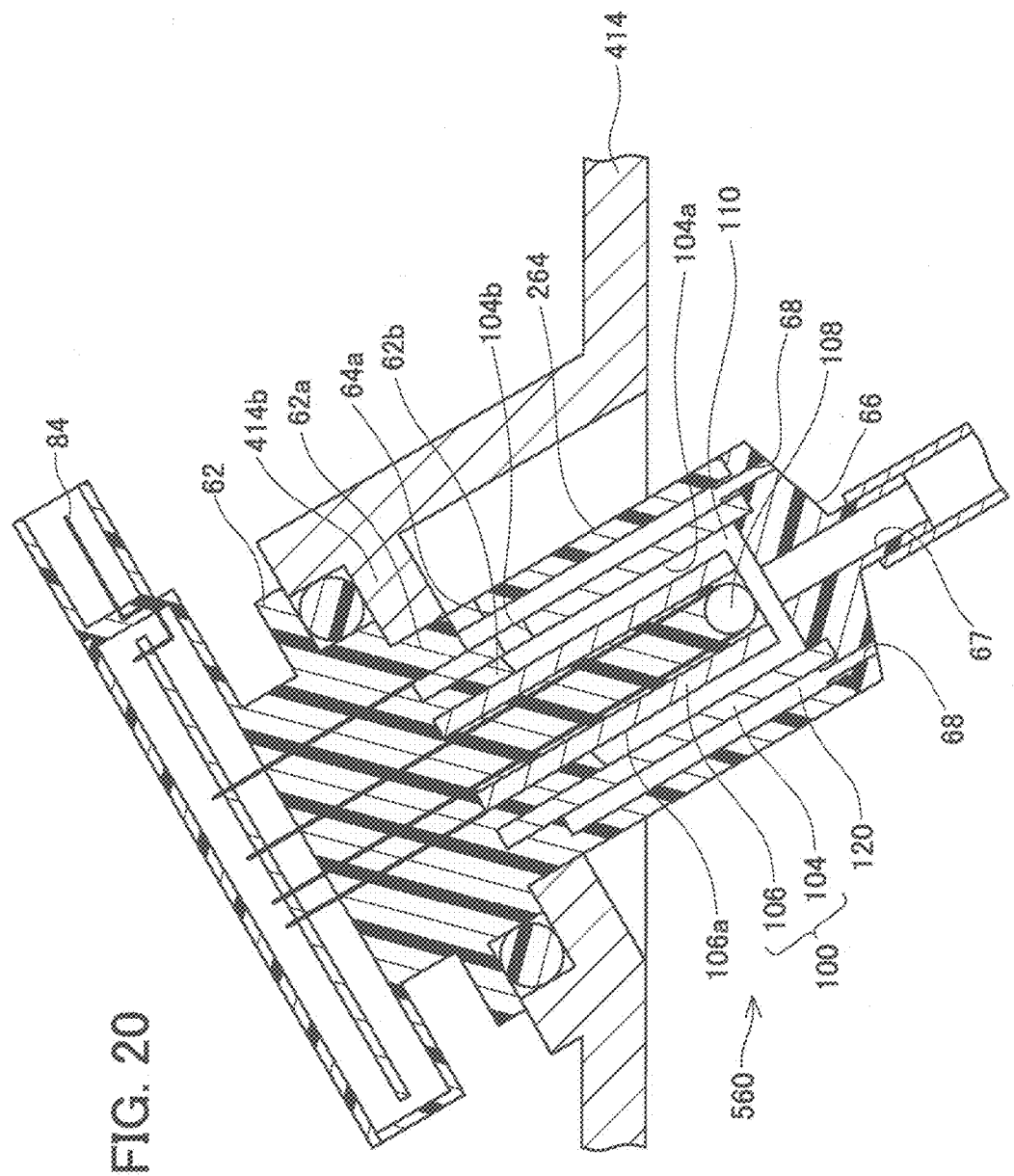
FIG. 20 shows a configuration of a liquid property sensor and control unit of a fifth embodiment.

A liquid property sensor 560 shown in FIG. 20 is placed on an inclined surface 414b of a set plate 414. As a result of this, the communication opening 64a is located directly above the communication opening 104b. The other components of the liquid property sensor 560 are the same as those of the liquid property sensor 260 of the second embodiment.

In the configuration of the present embodiment, the communication opening 104b opens upward. As a result of this, gas in the storage space 110 can smoothly pass through the communication opening 104b. Further, since the communication opening 64a is located directly above the communication opening 104b, gas discharged through the communication opening 104b can be properly discharged out of the liquid property sensor 560 through the communication 64a.

(Sixth Embodiment)

Points of difference between a liquid property sensor 660 of the sixth embodiment and the second embodiment are described with reference to FIG. 21. Components that are the same as those of the second embodiment are given the same reference signs as those of the second embodiment. The liquid property sensor 660 includes an electrode pair 100, an upper wall 62, a peripheral wall 264, a bottom wall 666, and a thermistor 108.

A lower surface of the support wall 62b of the upper 62 is located at the same level for the entire circumference thereof. The communication opening 64a in the peripheral wall 264 is located above the after-mentioned communication opening 667.

The communication opening 104b in the electrode 104 is disposed to be in the same direction as the communication opening 64a along a circumferential direction of the electrode 104.

The peripheral wall 264 is integrally attached to an upper surface of the bottom wall 666. Further, a lower portion of the electrode 104 is inserted in the upper surface of the bottom wall 666. This causes the bottom wall 666 to support a lower end of the electrode 104. There is a clearance between the bottom wall 666 and the lower end of the electrode 106.

The bottom wall 666 has a communication opening 668 bored through the center thereof from a lower surface of the bottom wall 666 to the upper surface of the bottom wall 666. The communication opening 668 is disposed coaxially with the electrode 106 and faces the lower end of the electrode 106. Further, the bottom wall 666 has a communication opening 667 bored therethrough between the electrode 106 and the peripheral wall 264 from the lower surface of the bottom wall 666 to the upper surface of the bottom wall 666. The communication opening 667 communicates with the release pipe 52.

The storage space 110 is defined by the opposing surface 104a, the opposing surface 106a, the upper wall 62, particularly the lower surface of the support wall 62b, and the upper surface of the bottom wall 666. Further, the storage space 120 is defined by the outer circumferential surface of the electrode 104, the inner circumferential surface of the electrode 102, the upper wall 62, particularly the lower surface of the support wall 62a, and the upper surface of the bottom wall 666.

Figure 21:
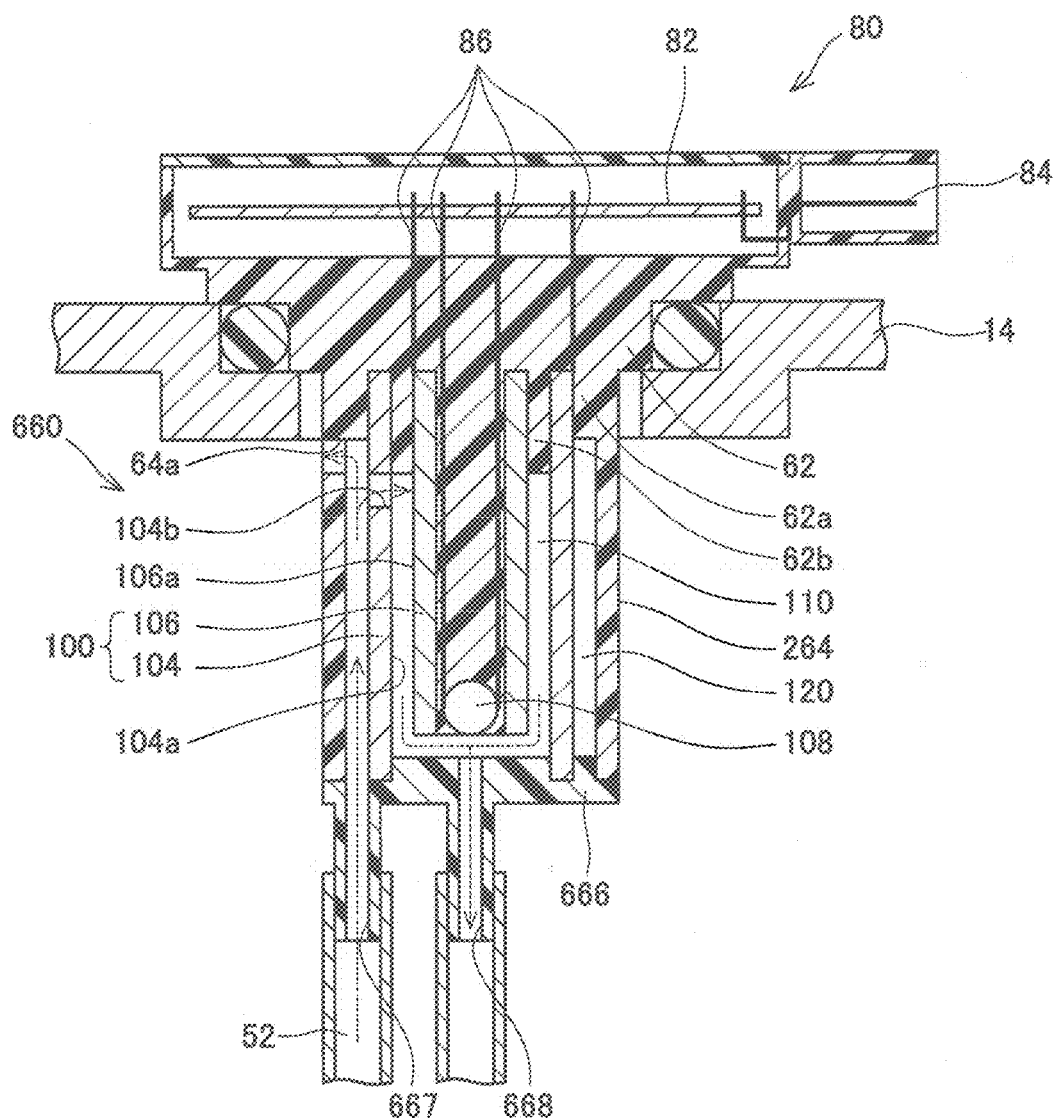
FIG. 21 shows a configuration of a liquid property sensor and control unit of a sixth embodiment.

As indicated by arrows in FIG. 21, the fuel from the release pipe 52 flows into the storage space 120 through the communication opening 667. The fuel inside of the storage space 120 flows from bottom to top through the storage space 120 by passing through a space between the peripheral wall 264 and the electrode 104. Then, a portion of the fuel flows from the storage space 120 into the storage space 110 through the communication opening 104b, and the other portion of the fuel flows out of the liquid property sensor 660 through the communication opening 64a. The fuel having flowed into the storage space 110 flows from top to bottom through the storage space 110 to be released out of the storage space 110 through the communication opening 668. This configuration allows gas in the fuel having flowed into the storage space 120 to be discharged out of the storage space 120 through the communication opening 64a. This makes it possible to reduce bubbles in the fuel that flows into the storage space 110.

(Modifications of the Sixth Embodiment)

Figure 22:
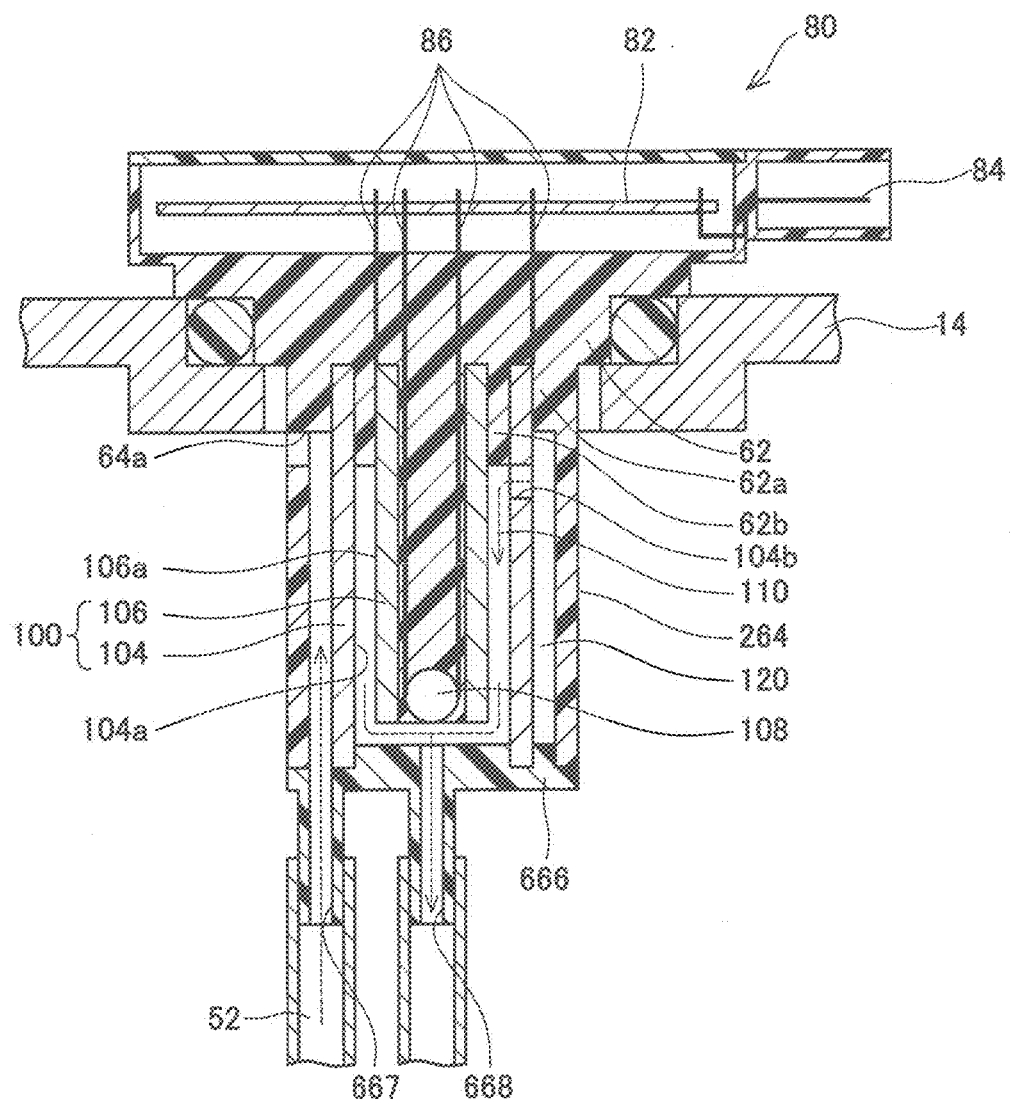
FIG. 22 shows a configuration of a liquid property sensor and control unit of a modification of the sixth embodiment.

(1) As shown in FIG. 22, the communication opening 104b in the electrode 104 is disposed to be in a direction opposite to the communication opening 64a along a circumferential direction of the electrode 104. This configuration allows the fuel having flowed in through the communication opening 667 to smoothly flow not only vertically but also circumferentially through the storage space 120 until it reaches the communication opening 64a. This configuration can inhibit the fuel from staying inside of the storage space 120.

Figure 23:
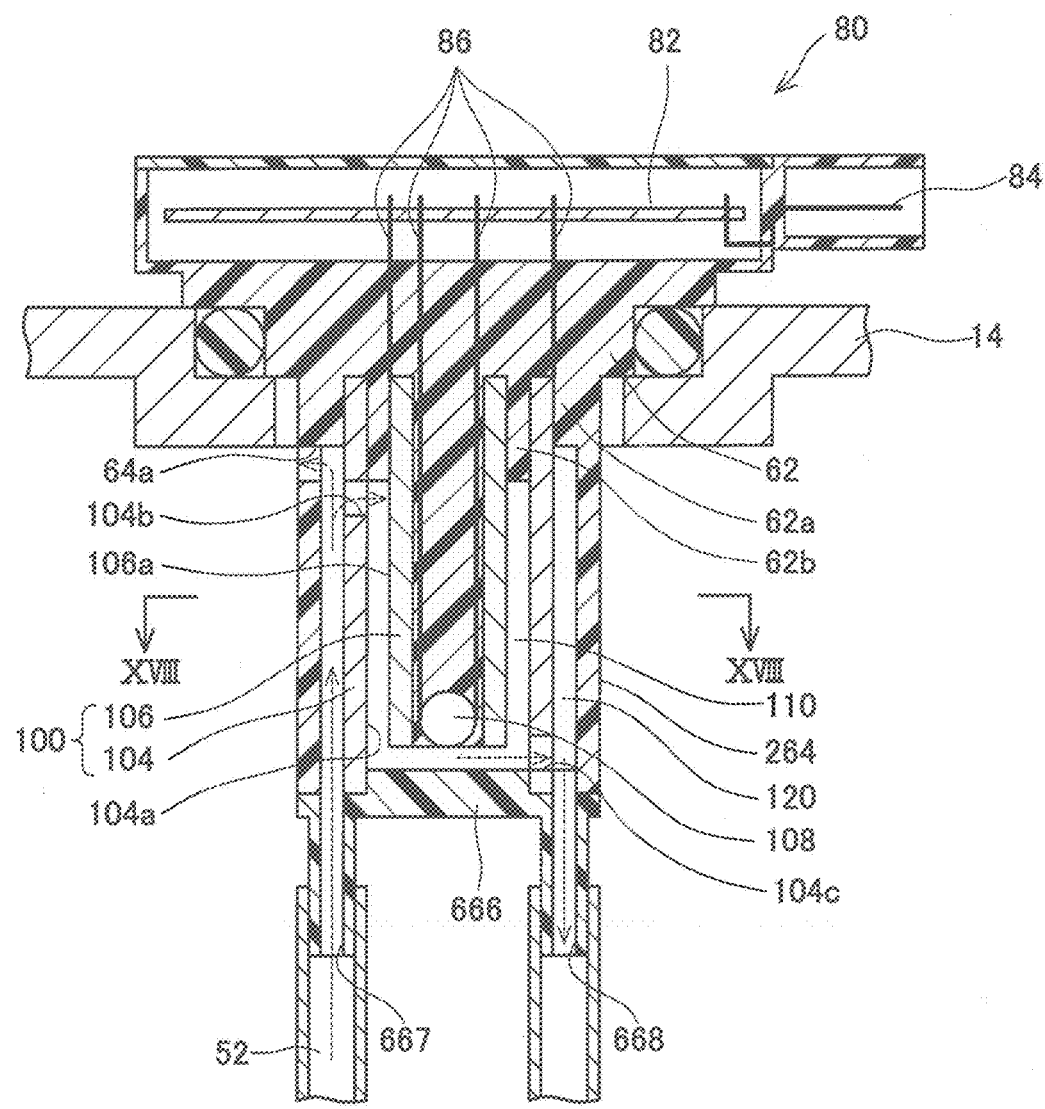
FIG. 23 shows a configuration of a liquid property sensor and control unit of a modification of the sixth embodiment.
Figure 24:
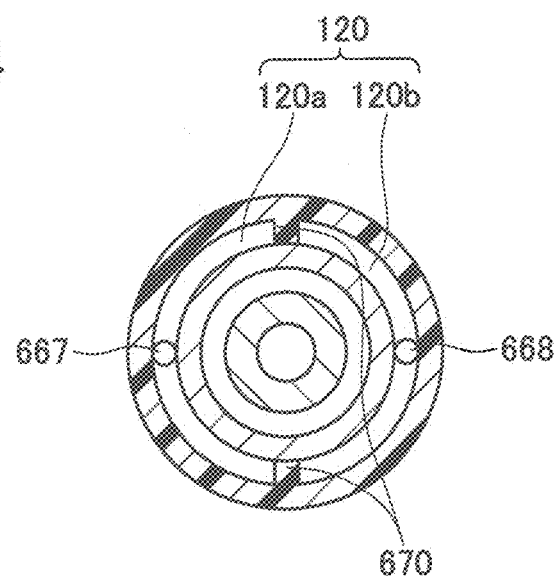
FIG. 24 shows a sectional view taken along cross-section XXIV-XXIV of FIG. 23.

(2) As shown in FIG. 23, the communication opening 668 through which the fuel is allowed to flow out of the liquid property sensor 660 from the storage space 110 may be disposed between the peripheral wall 264 and the electrode 104. Further, the electrode 104 may have a communication opening 104c disposed to be in a direction opposite to the communication openings 64a and 104b and communicating the storage space 110 and the storage space 120 along a circumferential direction of the electrode 104. The communication opening 104c may be disposed at the lower end of the storage space 110. As shown in FIG. 24, the storage space 120 may be divided by a dividing wall 670 into two spaces 120a and 120b. The communication opening 667 may communicate an inside of the space 120a and an outside of the space 120a. The communication opening 668 may communicate an inside of the space 120b and an outside of the space 120b. Fuel may flow into the space 120a through the communication opening 667 and flow into the storage space 110 through the communication opening 104b. The fuel inside of the storage space 110 may flow into the space 120b through the communication opening 104c disposed in the electrode 104 and flow from top to bottom through the space 120b to be discharged out of the liquid property sensor 660 through the communication opening 668. Alternatively, the storage space 120 may be divided by dividing walls 670 into three or more spaces. In this case, each of the spaces may communicate with at least one of another space, the storage space 110, and an outside of the liquid property sensor 660 by the communication opening. In the present modification, the communication opening 668 is an example of the "fifth communication opening".

Figure 25:
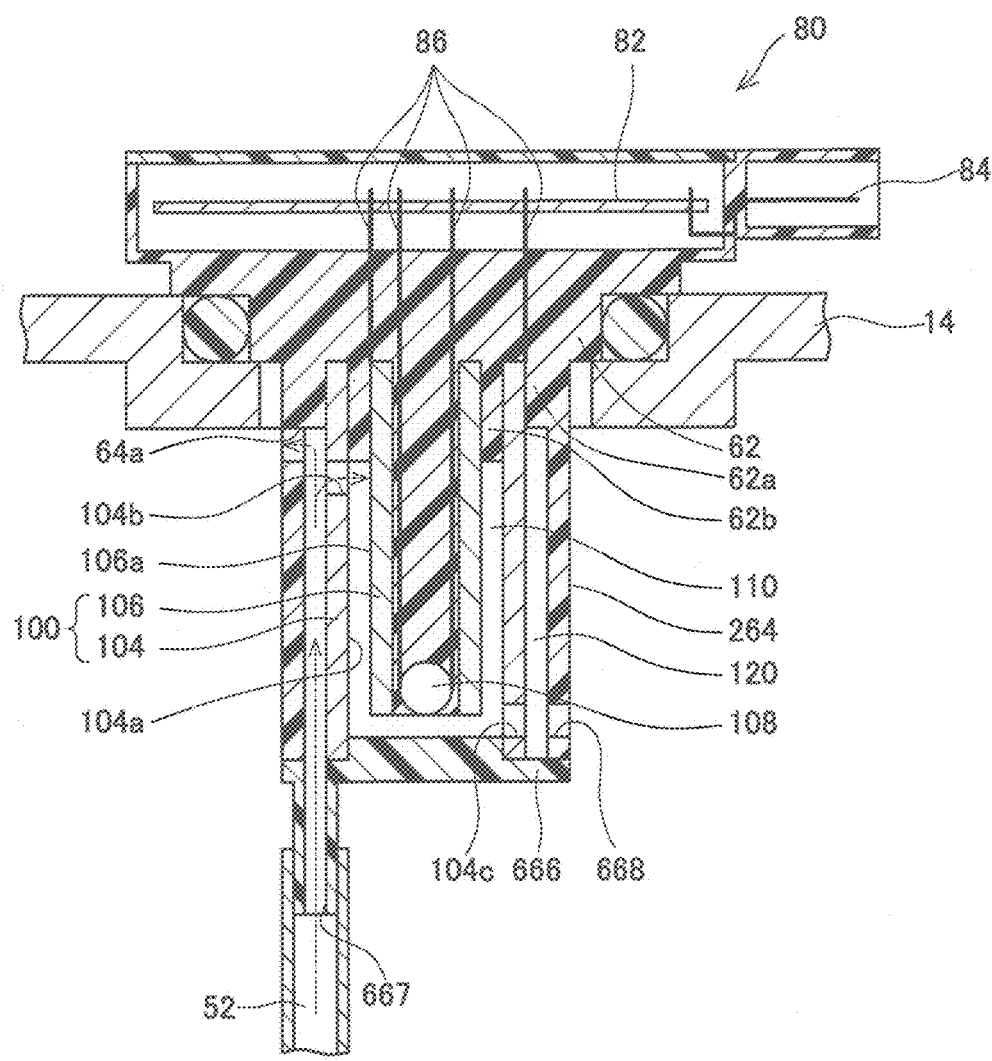
FIG. 25 shows a configuration of a liquid property sensor and control unit of a modification of the sixth embodiment.

(3) As shown in FIG. 25, the peripheral wall 64 may have a communication opening 668 disposed coaxially with the communication opening 104c.

(4) In FIGS. 23 and 25, the communication opening 104b and the communication opening 104c open in opposite directions with the central axis of the electrode 104 therebetween. However, the communication opening 104b and the communication opening 104c may be disposed so as not to be in the same place, i.e. so as to open in different directions along a circumferential direction of the electrode 104. For example, the communication opening 104c may be disposed to be in a place 90 degrees off the communication opening 104b along a circumferential direction of the electrode 104.

(Modifications)

(1) In each of the embodiments described above, the sensor device 2 uses the liquid property sensor 60 to detect the concentration of ethanol in fuel. However, the sensor device 2 may detect the degree of deterioration of fuel (e.g. the degree of oxidation of fuel), the liquid level of fuel, etc.

(2) The "liquid sensor" may be used for detecting a property of a liquid other than fuel, e.g. cooling water (e.g. the degree of deterioration, type, or liquid level of cooling water).

(3) In each of the embodiments described above, the release pipe 52 is connected to the pressure regulator 42. However, the release pipe 52 may branch off from the pipe 94 or may be connected to a vapor jet of the pump body 34.

(4) In each of the embodiments described above, the number of electrodes of the liquid property sensor 60 or the like is not limited to two or three. However, the liquid property sensor 60 or the like may include four or more electrodes.

(5) in each of the embodiments described above, the control circuit 82 detects the concentration of ethanol and the like with the capacitance of each electrode pair, i.e. the dielectric constant of fuel. However, the control circuit 82 may detect the concentration of ethanol with a value obtained with an electrode pair other than the capacitance of each electrode pair, e.g. the dielectric constant of fuel as obtained with an electrode pair.

(6) The liquid property sensor 60 or the like of each of the embodiments described above may include a temperature detecting element other than a thermistor so as to detect the temperature of fuel.

What is claimed is:

1. A liquid sensor comprising:
a first electrode comprising a first opposing surface;
a second electrode disposed inside the first electrode and comprising a second opposing surface opposing the first opposing surface with a clearance in between; and
a partition wall comprising a surface defining a storage space with the first opposing surface and the second opposing surface; wherein
one of the first electrode, the second electrode and the partition wall comprises a first communication opening communicating an inside of the storage space and an outside of the storage space and disposed at an upper portion of the storage space,
one of the first electrode, the second electrode and the partition wall comprises a second communication opening communicating the inside of the storage space and the outside of the storage space and disposed lower than the first communication opening; and
an opening direction of the first communication opening is different from an opening direction of the second communication opening; and
an outer wall covering the first electrode from the outside, wherein a clearance is disposed between the outer wall and the first electrode, and
the outer wall comprises:
a third communication opening communicating the clearance between the outer wall and the first electrode and an outside of the outer wall and disposed at an upper portion of the outer wall, and
a fourth communication opening communicating between the clearance between the outer wall and the first electrode and the outside of the outer wall and disposed at a lower portion of the outer wall.

2. The liquid sensor as in claim 1, wherein
the clearance between the outer wall and the first electrode communicates with the storage space via the first communication opening or the second communication opening, or a combination thereof.

3. The liquid sensor as in claim 2, wherein
the outer wall comprises:
a dividing wall dividing the clearance between the outer wall and the first electrode into a plurality of sections; and
a fifth communication opening communicating the clearance between the outer wall and the first electrode and the outside of the outer wall, wherein
a first section of the plurality of sections communicates with the outside of the outer wall via the fourth communication opening, with the storage space via the first communication opening, and with the outside of the outer wall via the third communication opening, and
a second section of the plurality of sections, being different from the first section, communicates with the outside of the outer wall via the fifth communication opening, and with the storage space via the second communication opening.

4. The liquid sensor as in claim 1, wherein
the outer wall is made of an electrically conductive material.

5. The liquid sensor as in claim 1, wherein
the partition wall comprises an upper wall posed at an upper end of the storage space, and
a surface of the upper wall defining the storage space is inclined upward toward the first communication opening.

6. The liquid sensor as in claim 1, further comprising:
a temperature sensor configured to detect a temperature of liquid.

7. The liquid sensor as in claim 6, wherein
the temperature sensor is disposed inside the second electrode and near the second communication opening.

8. The liquid sensor as in claim 7, wherein
of one end portion of the second electrode disposed near the second communication opening is narrower than a portion of the second electrode other than the one portion of the second electrode.

9. The liquid sensor as in claim 8, wherein
one of or both of the first electrode and the partition wall comprise an opposing surface opposing the one portion of the second electrode disposed near the second communication opening, and
the opposing surface has a shape formed along the one end portion of the second electrode disposed near the second communication opening.

10. A liquid sensor comprising:
a first electrode comprising a first opposing surface;
a second electrode disposed inside the first electrode and comprising a second opposing surface opposing the first opposing surface with a clearance in between; and a partition wall comprising a surface defining a storage space with the first opposing surface and the second opposing surface; wherein one of the first electrode, the second electrode and the partition wall comprises a first communication opening communicating an inside of the storage space and an outside of the storage space and disposed at an upper portion of the storage space, one of the first electrode, the second electrode and the partition wall comprises a second communication opening communicating the inside of the storage space and the outside of the storage space and disposed lower than the first communication opening, and an opening direction of the first communication opening is different from an opening direction of the second communication opening, wherein the partition wall comprises an upper wall disposed at an upper end of the storage space, and a surface of the upper wall defining the storage space is inclined upward toward the first communication opening.

11. A liquid sensor comprising:

a first electrode comprising a first opposing surface;

a second electrode disposed inside the first electrode and comprising a second opposing surface opposing the first opposing surface with a clearance in between; and a partition wall comprising a surface defining a storage space with the first opposing surface and the second opposing surface; wherein one of the first electrode, the second electrode and the partition wall comprises a first communication opening communicating an inside of the storage space and an outside of the storage space and disposed at an upper portion of the storage space, one of the first electrode, the second electrode and the partition wall comprises a second communication opening communicating the inside of the storage space and the outside of the storage space and disposed lower than the first communication opening, and an opening direction of the first communication opening is different from an opening direction of the second communication opening, wherein the first opposing surface and the second opposing surface extend by being inclined relative to a vertical direction.

12. The liquid sensor as in claim 11, wherein the first opposing surface and the second opposing surface extend horizontally.

* * * * *